United States Patent
Tang et al.

(10) Patent No.: US 9,081,071 B2
(45) Date of Patent: Jul. 14, 2015

(54) LONGEVITY OF HYPERPOLARIZED ENHANCED SIGNALS FOR $^1$H NMR SPECTROSCOPY

(71) Applicant: New York University, New York, NY (US)

(72) Inventors: Joel A. Tang, New York, NY (US); Francesca Gruppi, New York, NY (US); Roman Fleysher, New York, NY (US); Daniel K. Sodickson, New York, NY (US); James W. Canary, New York, NY (US); Alexej Jerschow, New York, NY (US)

(73) Assignee: New York University, New York, NY (US)

( * ) Notice: Subject to any disclaimer, the term of this patent is extended or adjusted under 35 U.S.C. 154(b) by 236 days.

(21) Appl. No.: 13/622,248

(22) Filed: Sep. 18, 2012

(65) Prior Publication Data

US 2013/0267036 A1 Oct. 10, 2013

Related U.S. Application Data

(63) Continuation-in-part of application No. PCT/US2011/029078, filed on Mar. 18, 2011.

(60) Provisional application No. 61/315,714, filed on Mar. 19, 2010.

(51) Int. Cl.
*G01N 24/00* (2006.01)
*G01R 33/46* (2006.01)
*G01N 24/08* (2006.01)
*G01R 33/28* (2006.01)

(52) U.S. Cl.
CPC ............... *G01R 33/46* (2013.01); *G01N 24/08* (2013.01); *G01R 33/282* (2013.01); *Y10T 436/24* (2015.01)

(58) Field of Classification Search
CPC ..................................................... Y10T 436/24
See application file for complete search history.

(56) References Cited

U.S. PATENT DOCUMENTS

2008/0204014 A1 8/2008 Desvaux et al.
2009/0016964 A1 1/2009 Kalechofsky et al.

FOREIGN PATENT DOCUMENTS

WO  WO 2009-046457 A2  4/2009

OTHER PUBLICATIONS

Aguilar, J. A. et al. Only para-hydrogen spectroscopy (OPSY), a technique for the selective observation of para-hydrogen enhanced NMR signals, 2007, Chemical Communications, 2007, pp. 1183-1185.*

(Continued)

*Primary Examiner* — Robert Xu
(74) *Attorney, Agent, or Firm* — Foley & Lardner LLP

(57) ABSTRACT

A method and system for providing an article of manufacture with increased longevity of hyperpolarized $^1$H signals (and other species) for NMR spectroscopy and MRI. The method involves providing a material including a molecular species susceptible of NMR spectroscopy, by providing parahydrogen (and other appropriate species) to disperse within the material/solvent to establish increased longevity of the NMR signals. The material can be in a solution with a surfactant and catalysts added to enhance the persistence of parahydrogen (or other species) in the form of enhanced solubility, microbubbles or micelles and resultant hydrogenation (or other species) of the material.

6 Claims, 26 Drawing Sheets

(56) References Cited

OTHER PUBLICATIONS

PCT International Search Report, International Application No. PCT/US2011/029078, dated Nov. 29, 2011, 2 pages.

Tang et al., "Extended para-hydrogenation monitored by NMR spectroscopy", *Chem. Commun.*, (2011), pp. 958-960, vol. 47, The Royal Society of Chemistry.

* cited by examiner

Vertical Scale
x 30

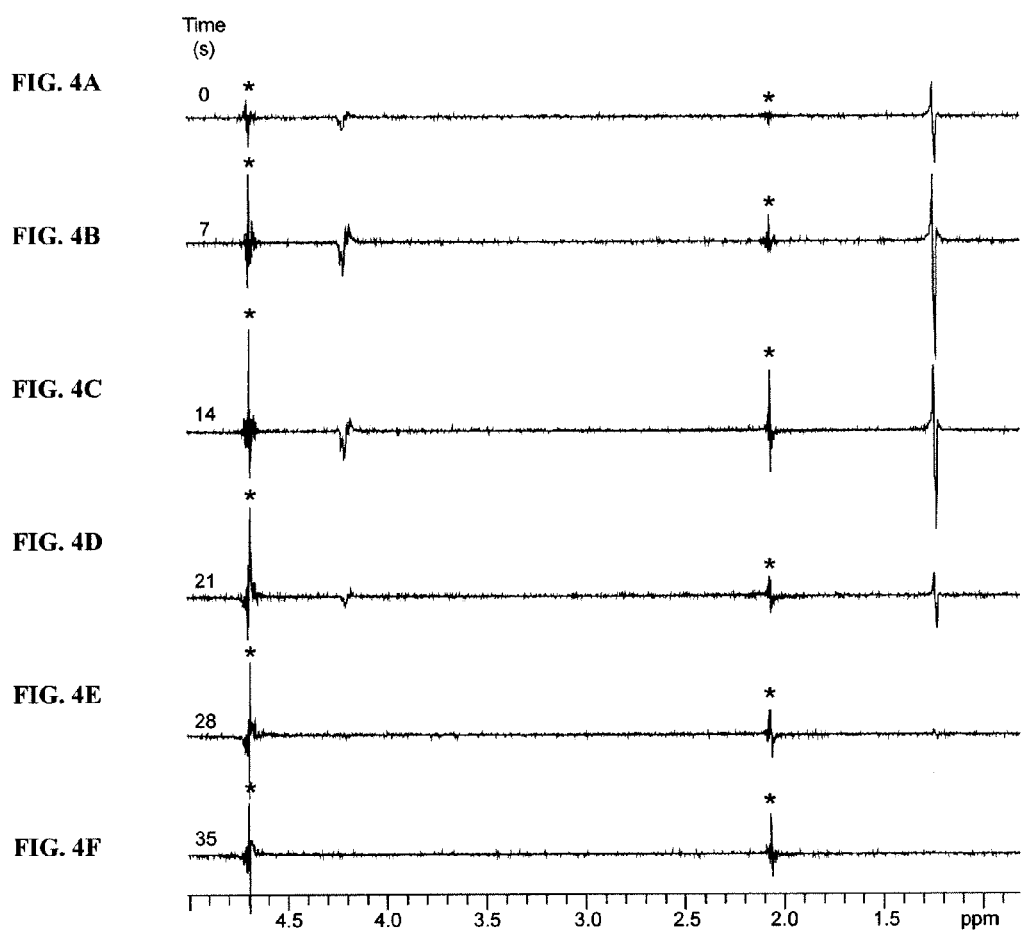

FIG. 5A
FIG. 5B
FIG. 5C
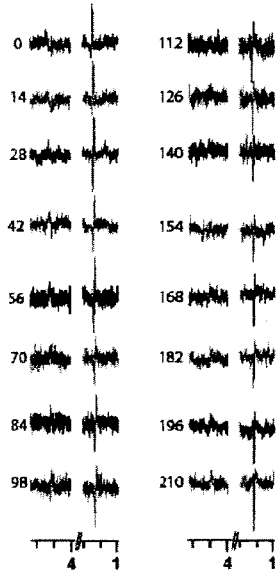
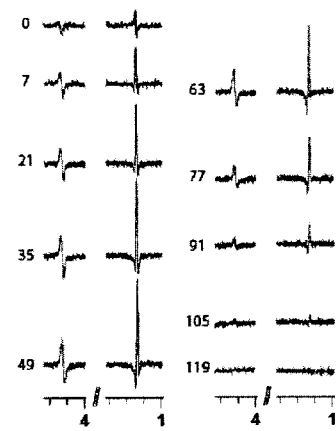
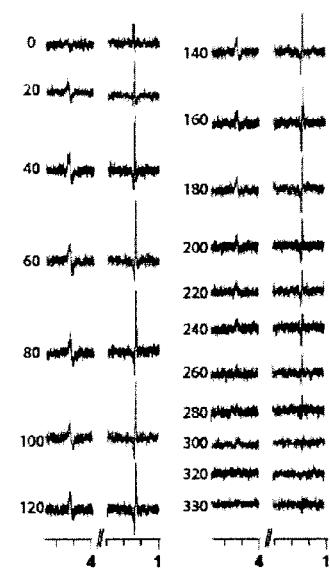

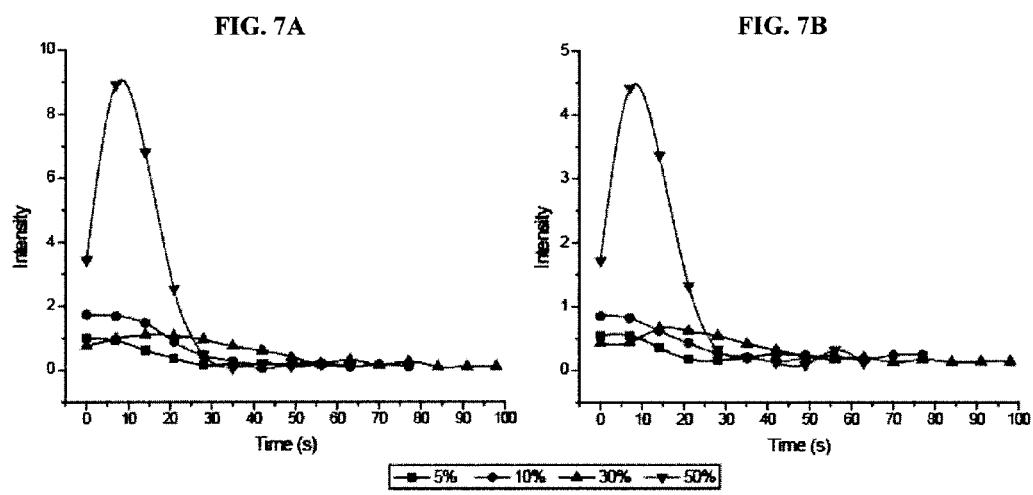

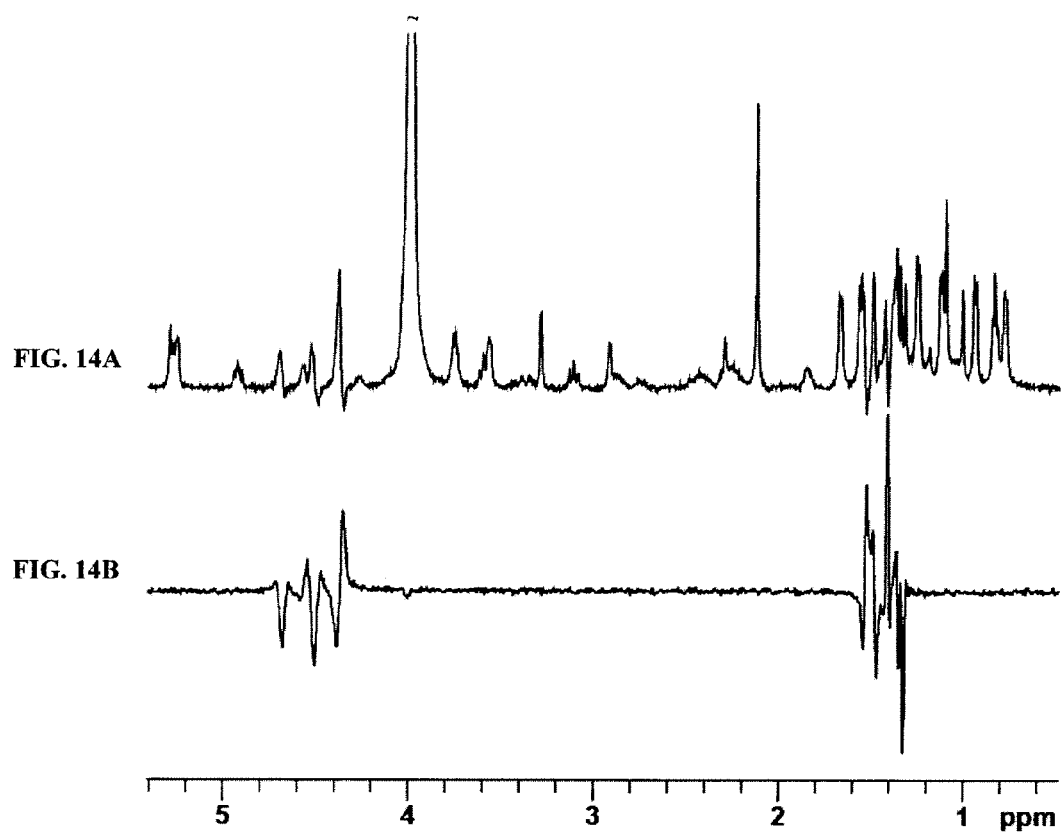

LONGEVITY OF HYPERPOLARIZED ENHANCED SIGNALS FOR $^1$H NMR SPECTROSCOPY

The application is a continuation-in-part of International Patent Application Serial No.: PCT/US2011/029078, filed Mar. 18, 2011, which claims priority to U.S. Provisional Patent Application Ser. No. 61/315,714, filed Mar. 19, 2010, the disclosure of which are expressly incorporated herein by reference in their entirety.

FIELD OF THE INVENTION

The present invention relates to improving the longevity and signal strength of hyperpolarized enhanced signals for $^1$H NMR spectroscopy. More particularly, the invention relates to creating enhanced signal longevity for $^1$H NMR spectroscopy by providing enhanced persistence of parahydrogen in a medium containing a material with a molecular species which is to be analyzed by $^1$H NMR spectroscopy.

BACKGROUND OF THE INVENTION

Nuclear magnetic resonance (NMR) spectroscopy is a versatile analytical technique used in a broad range of disciplines, ranging from materials science, chemical synthesis, catalysis, structural and cell biology, oil-well logging, metabolomics and metabonomics, and in vivo spectroscopy and imaging. Its great strength resides on its site selectivity and sensitivity to changes in local environments. Experiments can be tailored to monitor specific aspects of the molecules under study, such as the local electronic environment, the topology, distances and angles in molecules, their motional properties, and intermolecular interactions.

The study of naturally occurring biomolecules with NMR has always been of great interest to elucidate structure, reactivity and properties of functional groups in peptides. However, with large molecules, interpretation of NMR spectra may be difficult, in particular for the analysis of specific fragments. In peptides or proteins, the capability of visualizing sites of interest is reduced due to overlapping resonances or reduced intensity. Multidimensional NMR experiments are often used to discriminate these sites from the rest of the molecule, but sometimes the spectrum can still contain obscured peaks and a complete characterization is difficult. Isotopic labeling methods are also utilized; however, the labeling process may be complicated for naturally occurring biomolecules. An alternative method to make the peaks more prevalent is by using a hyperpolarized label.

Many hyperpolarization techniques are being used to study biomolecules such as hyperpolarized Xe for the study of protein interactions and binding dynamics, and exploiting the difference in chemical shift of the gases. Dynamic nuclear polarization (DNP) methods including (photo-) chemically induced and high-field experiments are used to obtain information including structural features, and folding dynamics of proteins. Although these methods are highly effective, the experiments involve complicated setups and difficult implementation.

The phenomenal site-selectivity exhibited by NMR spectroscopy is also related to one of its principal drawbacks—detection sensitivity. Several avenues for improving sensitivity have been identified, including dynamic nuclear polarization, optical pumping, and parahydrogen (p-$H_2$) induced polarization (PHIP) techniques. Over the last two decades, prior art PHIP experiments including their specific implementations in the form of the well-known PASADENA and ALTADENA work, have been developed to improve the sensitivity of NMR by a factor of $10^4$ to $10^5$. The polarization can be incorporated into the molecular structure in two ways: 1. The SABRE method where the polarization is exchanged from the para-hydrogen to the target molecule via a catalytic intermediate; or 2. Through a hydrogenation reaction. Although the former method achieves polarization transfer without changing the chemical structure, it may not be easy to select specific sites and has only been shown to be effective on relatively small specific molecules. Hydrogenation with p-$H_2$, i.e. ALTADENA and PASADENA experiments, are fairly easy to implement and can be performed on any sample possessing an asymmetric multiple bond. One of the limitations of any form of proton polarization enhancement is that the signal will last only as long as typical $T_1$ relaxation times in the molecules. This makes them difficult to implement for some experiments such as diffusion experiments and magnetic resonance imaging using hyperpolarized contrast agents, because they may require many seconds for molecular distribution within the system to occur. Bargon et al. have shown that the lifetime of the hyperpolarization in low magnetic fields can exist for 300 s.

Carravetta et al. and others in the prior art have shown that one can store the nuclear spin order using low field nuclear spin singlet states for times much longer than the $T_1$ relaxation time constants. However, such ingenious approaches will be practical only for a select subset of systems and they require quick field cycling between high and low magnetic fields. The long longitudinal relaxation time of $^{13}$C nuclei has also been exploited for long lived polarized signals. This nucleus provides a means for storing the polarization for longer times, since $T_1$ of $^{13}$C is typically much longer than for $^1$H spins. However, with the extremely low natural abundance of $^{13}$C (<1.1%), enriched compounds are required, and the efficient transfer will very much depend on the coupling patterns within the molecules.

Another limitation is that the high polarization can typically only be used in conjunction with small flip angle pulses, otherwise the available signal quickly dephases on the order of $T_2$. With a large flip angle, the polarization would have to be replenished with p-$H_2$ between one experiment and the next.

Therefore, the benefit of further extending the time within which hyperpolarized $^1$H signals could be observed would provide a broad range of new applications.

SUMMARY OF THE INVENTION

A method, system and article of manufacture are provided for allowing the detection of a hyperpolarized $^1$H NMR signal well after the initiation of the reaction process by improving the dispersion of hydrogen gas in a fluid, such as an aqueous containing medium. This invention can be generalized to other species, such as, but not limited to $^2$H, $^{13}$C, $^{15}$N, $^{31}$P, $^6$Li, $^{19}$F and other species susceptible to increase in the species relaxation time using the method of the invention. In a preferred embodiment, enhanced solubility, micelles or "microbubbles" are provided as hydrogen storage and sources of hydrogenation in the solution that then hydrogenates the material which contains a desired molecular species for analysis by NMR spectroscopy and also by MRI techniques (hereinafter throughout the application and claims, "NMR" shall also include MRI techniques as well). As an example, the hydrogenation of methyl 2-acetamidoacrylate to methyl 2-acetamidopropanoate is used to examine this methodology because of this material's short reaction time and high product yield.

In another aspect of the invention, the current reaction substrate methyl 2-acetamidoacrylate is a precursor to alanine. The material can be incorporated into a peptide that upon reaction with p-$H_2$, would yield a hyperpolarized peptide that could be followed by MRI analysis due to the high signal from hyperpolarization. Peptides or proteins containing alanine could be produced, and other amino acid precursors can easily be envisioned. Potential peptides that could be produced by this method include hormones, neuropeptides, amyloid peptides, therapeutic peptides, antihypertensive peptides, and many others. Nearly any protein could be labeled with p-$H_2$ in this manner, allowing for study of protein structure and receptor-substrate interactions by NMR or biodistribution and metabolism by MRI or spectroscopy. Additionally, many other substrates are conceivable. Nearly any molecule containing two vicinal hydrogen atoms (i.e., containing the substructure H—C—C—H) can be labeled by p-$H_2$ in a similar manner to the method described hereinafter.

The control and quantity of the release of hydrogen gas into solution is investigated through a variety of ways, including the variation of surfactant concentration, polarity of solvent, the addition of additives to the reaction, and the adjustment of parahydrogen bubble sizes. As a result, one may observe continuously hyperpolarized signals from the sample material at times much longer than $T_1$.

The above aspects and features, objects and advantages of the present invention will be more clearly understood from the following detailed description taken in conjunction with the accompanying drawings described below.

BRIEF DESCRIPTION OF THE DRAWINGS

FIGS. 4A-4F show $^1$H NMR spectra of a solution containing 21 mM methyl 2-acetamidoacrylate, 11 mM SDS and 1.1 mM catalyst in 25% (v/v) MeOD after bubbling with p-$H_2$ gas acquired using the OPSY sequence wherein for each spectrum of FIGS. 4A-4F data was collected in 7 s intervals as noted from the times on the left and resonances marked with an asterisk (*) denote thermal peaks that were not completely suppressed by the OPSY sequence;

FIG. 5A shows $^1$H NMR spectra of a solution containing 21 mM methyl 2-acetamidoacrylate, 11 mM SDS and 1.1 mM catalyst in 25% (v/v) MeOD acquired after shaking the NMR tube the fifth time; FIG. 5B shows spectra acquired after the sample is bubbled a second time; and FIG. 5C shows spectra acquired, taken every 10 s, after the sample is shaken again for the seventh time after the second bubbling procedure; only the peaks at 1.2 and 4.2 ppm are shown and not all spectra are given for clarity and the numbers on the left of each spectrum are the times in seconds at which they were acquired after experiment is initiated;

FIG. 7A shows a plot of signal intensity as a function of time for the hyperpolarized peaks at 1.2 ppm and FIG. 7B for 4.2 ppm for samples with different SDS concentrations after the initial bubbling of the solution with p-$H_2$; the intensities of each time set is with respect to the signal intensity of the first spectrum (t=0 s) acquired with the 1.07 mM SDS sample;

FIGS. 14A-B shows a $^1$H NMR spectra comparison using (A) single pulse and (B) OPSY sequences.

6.27 ppm with a strong signal intensity, corresponds to Ala-4 CH and Thr-12 CH. An examination of the 3D thiostrepton structure shows that the distance between Ala-4 CH and Thr-12 CH is only 2.26 Å. The short distance between the two protons explains well the strong signal observed in the ROESY spectrum. The region around δ=1.37 ppm does not show any cross peaks. This provides a reasonable explanation because in the 3D structure the methyl group is indeed pointing away from the core region of thiostrepton. No cross peaks were observed between Ala-4 and Ala-16/Ala-17.

Figure 22:
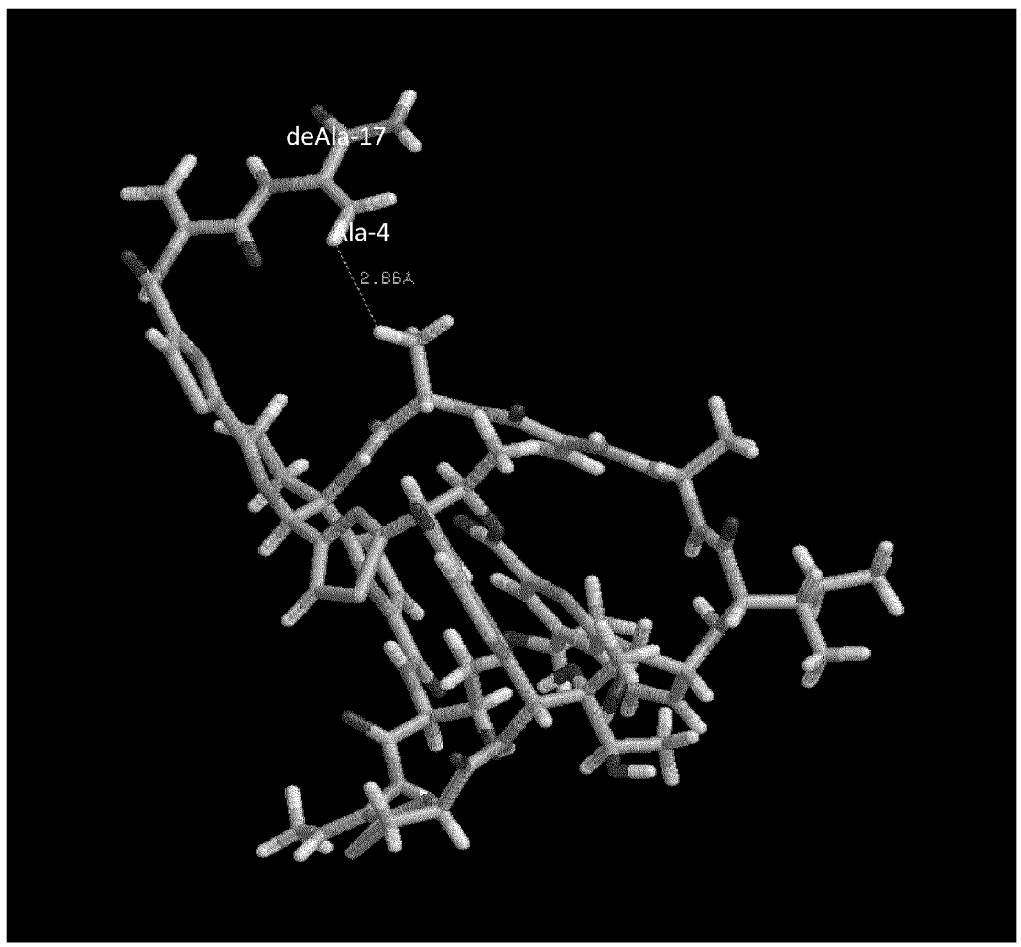

FIG. 22 is a RasMol (rosmol.org, Windows Version 2.7.5.2) molecular model illustrating the possible proximity of Ala-4 and deAla-17 after sigma-bond rotations of the tail.

Figure 23:
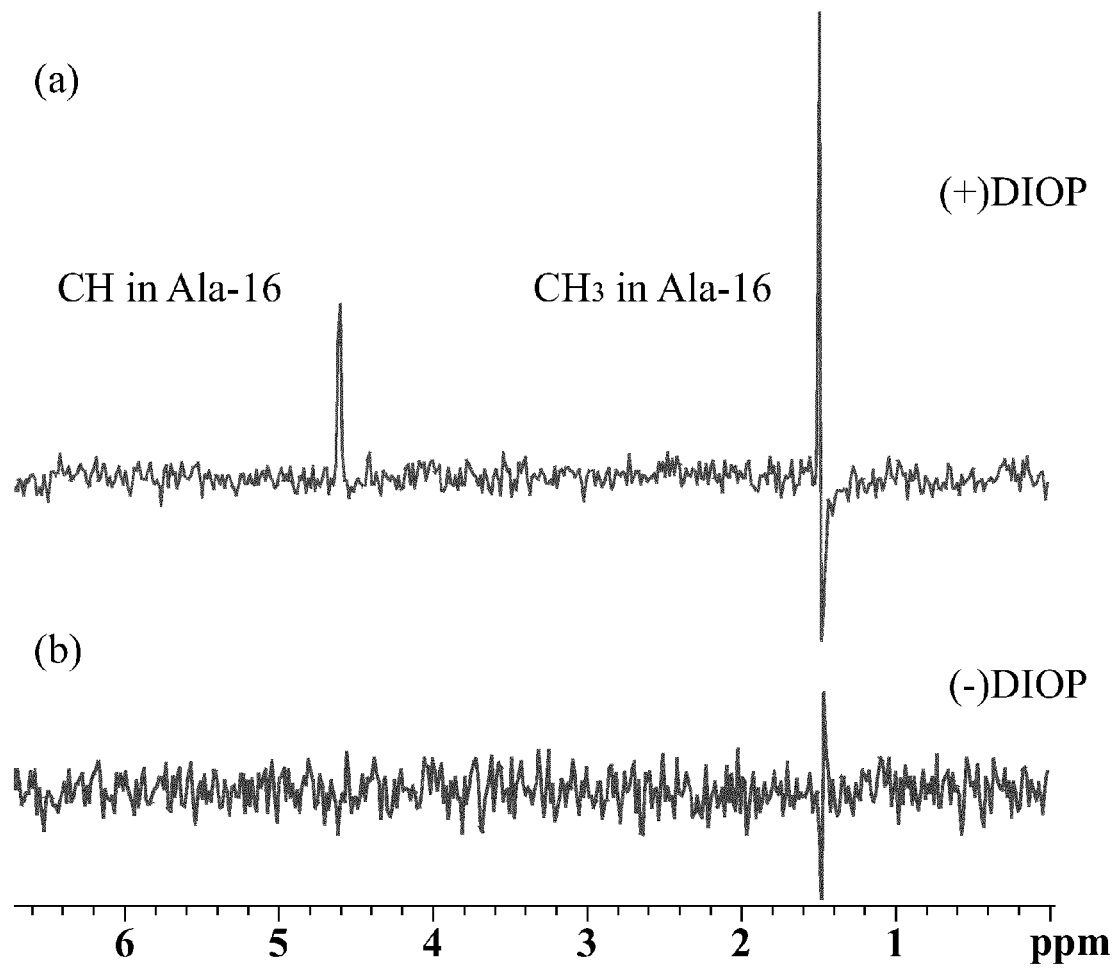

FIGS. 23A-B are a OPSY spectra of Thiostrepton derivative (Compound 2) hydrogenated with (A) catalyst with (+) DIOP; (B) catalyst with (−) DIOP.

FIGS. 24A-C are a $^1$H NMR spectra of hydrogenated thiostrepton: (A) hydrogenated with [Rh(COD)(+DIOP)]BF$_4$; (B) [Rh(COD)(−DIOP)]BF$_4$ using OP SY sequence; (C) thermal spectrum with [Rh(COD)(−DIOP)]BF$_4$.

Figure 25:
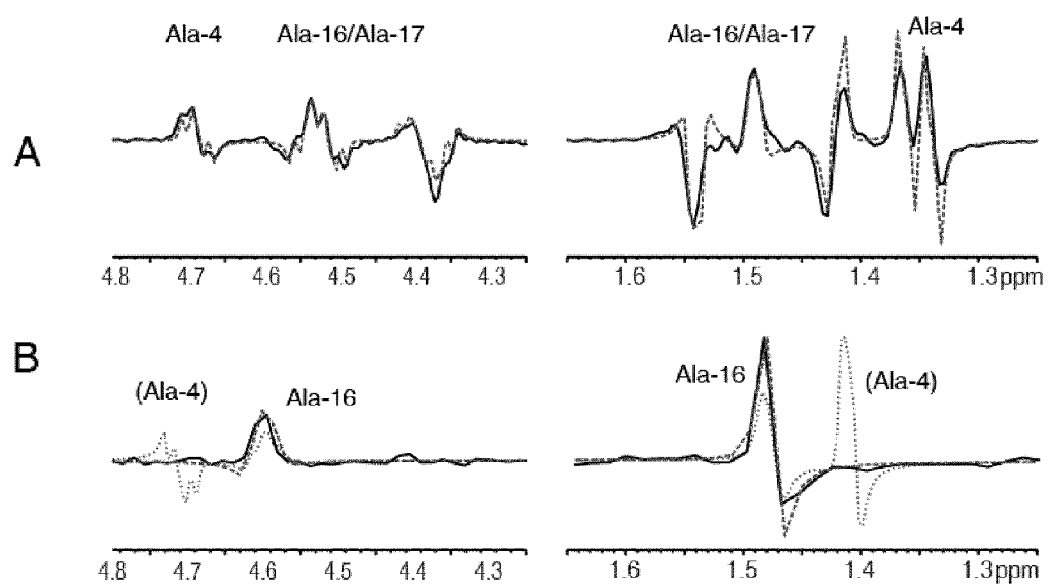

FIGS. 25A-B are an expanded spectra in the regions of δ=4.1-4.8 ppm and δ=1.2-1.7 ppm. (A) Hydrogenation of 1 (forming 4) using (+)DIOP; (B) hydrogenation of 2 (forming 6) using (+)DIOP. Black solid line, experimental OPSY spectra; red dashed line, simulated OPSY spectra; green dotted line, simulated OPSY spectra assuming there is hyperpolarization transfer to Ala-4. The disagreement between experiment and simulation indicates that in compound 6 there is no transfer to Ala-4.

Figure 26:
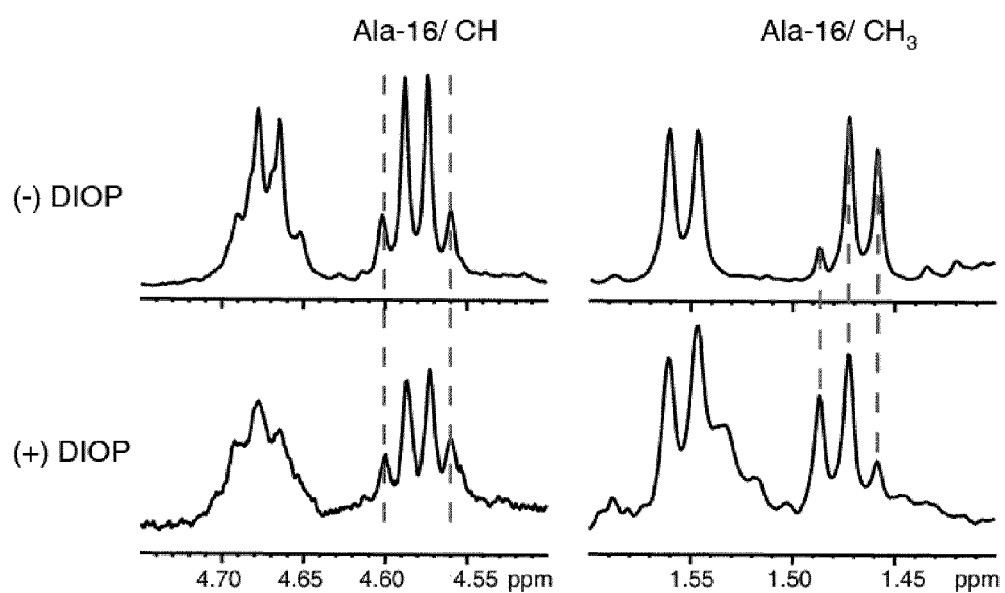

FIG. 26 illustrates the methyl and methine regions of the $^1$H NMR spectra of 6.

DETAILED DESCRIPTION OF PREFERRED EMBODIMENTS

Figure 1A:
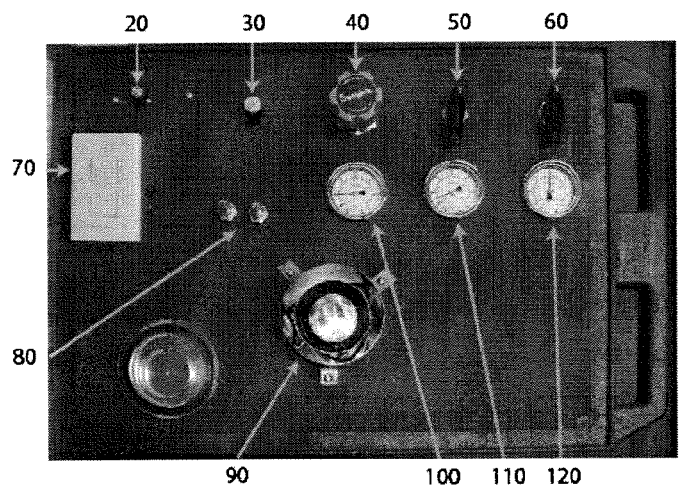
FIG. 1A shows a top view of an apparatus used for generating p-$H_2$ gas.
Figure 1B:
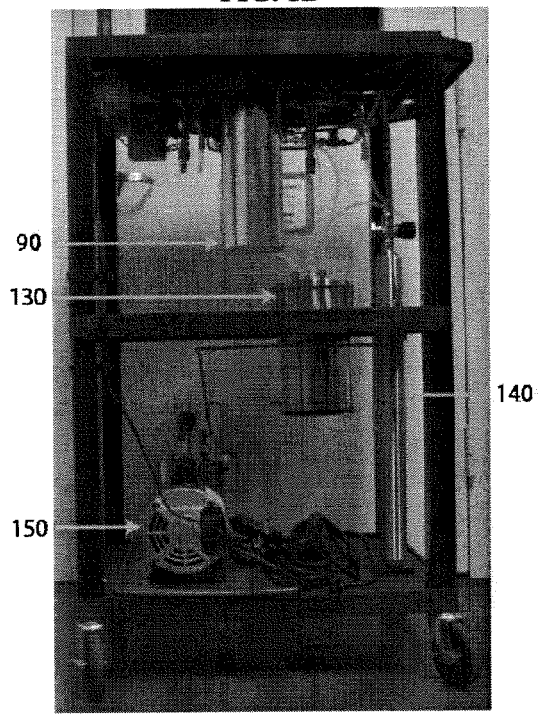
FIG. 1B shows a side view of the apparatus of FIG. 1A.
Figure 1C:
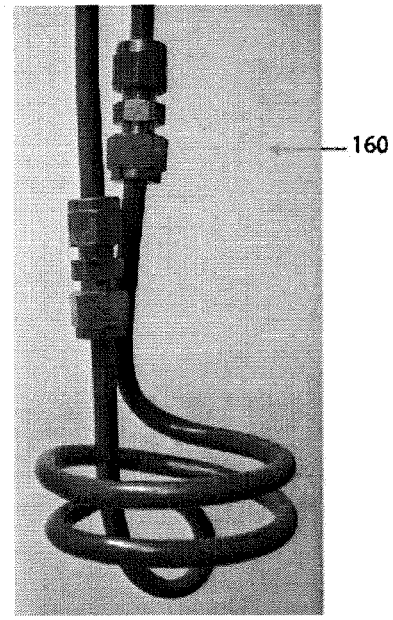
FIG. 1C shows a copper coil that is submerged in liquid $N_2$ which contains the catalyst for the conversion of o-$H_2$ to p-$H_2$.
Figure 2A:
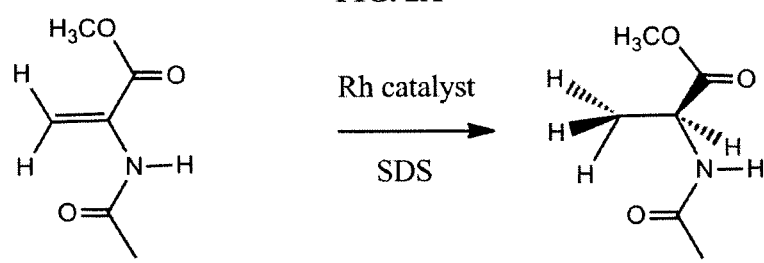
FIG. 2A shows the reaction scheme for homogeneous hydrogenation and FIG. 2B shows the SDS structure.
Figure 2B:
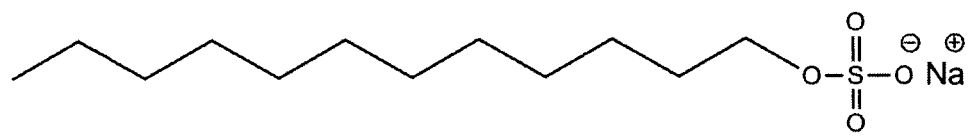

A method and system 10 shown in FIGS. 1A and 1B can provide a method for continuously supplying H$_2$ gas for a hydrogenation reaction, for quantifying the reaction progress and for increasing the longevity of the $^1$H NMR signal for measurement and analysis via para-hydrogen induced polarization-enhanced NMR spectroscopy. The system 10 includes timing regulator 20, gas flow regulator 30, gas pressure reglator 40, H$_2$ gas valve 50, vacuum valve 60, on/off switch 70, inlet and outlet ports 80, μ-metal shield 90, pressure gauge 100, gas gauge 110, vacuum gauge 120, liquid N$_2$ container 130, H$_2$ gas canister 140, and vacuum pump 150. In FIG. 1C is shown copper tube 160 that is submerged in liquid N$_2$ which contains catalyst for conversion of orthohydrogen (o-H$_2$) to p-H$_2$. The hyperpolarization apparatus (10) is filled with H$_2$ gas and stored in a gas cylinder (140) to a pressure of 100 psi indicated on gauge 110. When the gas is released into the system, the gas gets converted from —H$_2$ to p-H$_2$ when inside the copper coil containing an activated catalyst. This coil is submerged in liquid N$_2$ which is stored in a canister 130. To introduce the gas into the sample container (NMR tube), dials 20 (timing) and 30 (flow regulator) are set such that a continuous flow of p-H$_2$ gas is released for 10 seconds at a pressure of 10 psi set by the pressure regulator (40) and the gauge 100. The gas is released through ports 80 and controlled by switch 70. Where the reaction is to occur at low magnetic fields, the NMR tube could be placed within a μ-metal shield (90) and p-H$_2$ gas could be bubbled through the sample. To replenish the gas cylinder 140 with H$_2$ gas, dial 50 is closed to keep the system beyond the copper coil isolated. A vacuum pump (150) is used to remove any air that is trapped in tubing when connecting 10 to the main H$_2$ gas source. The vacuum is isolated between the 10 and the main H$_2$ source using dial 60 and the pressure is monitored using gauge 120.

The method and system also provides an article of manufacture in the form of a hydrogenated material suitable for extended term $^1$H NMR analysis. The procedure is demonstrated by studying the hydrogenation of the water-soluble compound methyl 2-acetamidoacrylate with p-H$_2$. The hyperpolarization apparatus (10) is filled with H$_2$ gas and stored in a gas cylinder (140) to a pressure of 100 psi indicated on gauge 110. When the gas is released into the system, the gas gets converted from —H$_2$ to p-H$_2$ when inside the copper coil containing an activated catalyst. This coil is submerged in liquid N$_2$ which is stored in canister 130. To introduce the gas into the sample container (NMR tube), dials 20 (timing) and 30 (flow regulator) are set such that a continuous flow of p-H$_2$ gas is released for 10 seconds at a pressure of 10 psi set by the pressure regulator (40) and the gauge 100. The gas is released through ports 80 and controlled by switch 70. For experiment requiring the reaction to occur at low magnetic fields, the NMR tube could be placed within a μ-metal shield (90) and p-H$_2$ gas could be bubbled through the sample. To replenish 140 with H$_2$ gas, dial 50 is closed to keep the system beyond the copper coil isolated. A vacuum pump (150) is used to remove any air that is trapped in tubing when connecting 10 to the main H$_2$ gas source. The vacuum is isolated between the 10 and the main H$_2$ source using dial 60 and the pressure is monitored using gauge 120.

Figure 3A:
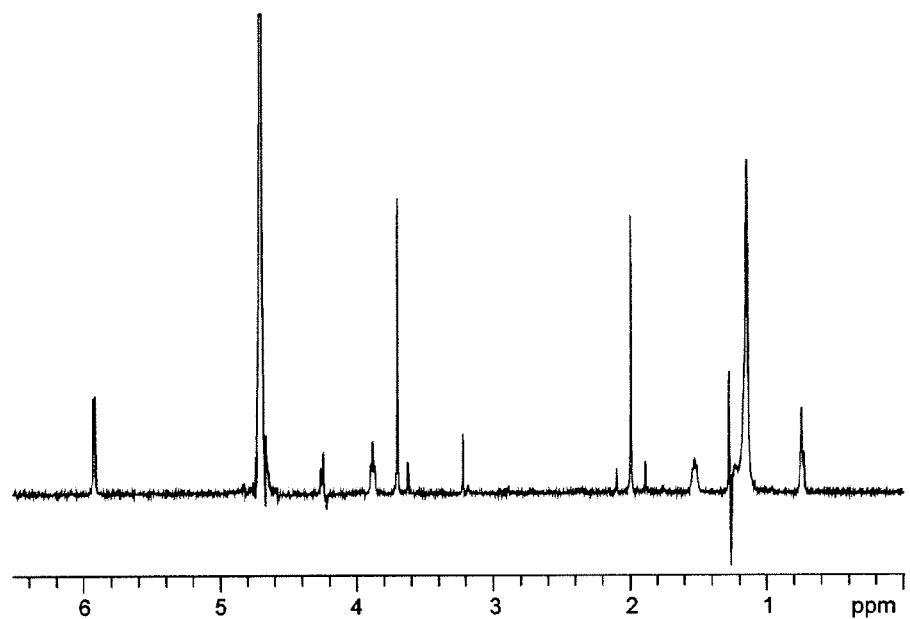
FIG. 3A shows $^1$H NMR spectra of a solution containing 21 mM methyl 2-acetamidoacrylate, 11 mM SDS and 1.1 mM catalyst in 25% (v/v) MeOD after bubbling with p-$H_2$ gas acquired using single pulse
Figure 3B:
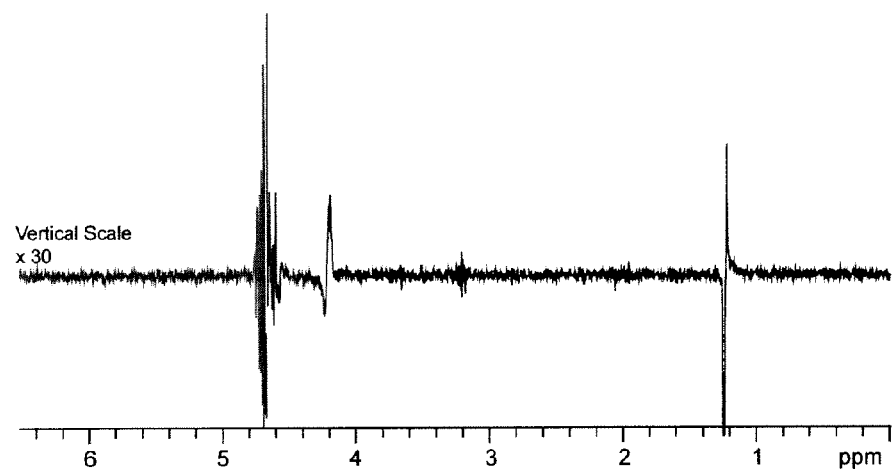
FIG. 3B shows results after only para-hydrogen spectroscopy (OPSY) experiments.

Bubbling p-H$_2$ through a solution of methyl 2-acetamidoacrylate (21×10$^{-3}$ M), SDS (11×10$^{-3}$ M) and Rh catalyst (1.1×10$^{-3}$ M) in 25% (v/v) MeOD in D$_2$O resulted in two signals enhanced by hyperpolarization (FIG. 3A). The methyl and ethylene groups of methyl 2-acetamidopropanoate at 1.2 and 4.2 ppm, respectively, showed the characteristic line shape of a polarization-enhanced signal. Using the only para-hydrogen spectroscopy (OPSY) sequence, nearly all of the thermal peaks were suppressed, leaving only the hyperpolarized signals (FIG. 3B).

Sequential experiments were perfoinied to examine the extent to which the hyperpolarized signal remained observable. In FIGS. 4A-4F, after purging the solution with p-H$_2$ gas for 15 seconds, the hyperpolarized signals at 1.2 and 4.2 ppm can be seen almost 30 seconds after the initiation of the NMR OPSY experiment. The times required to bring the sample to the spectrometer and lower it into the liquids NMR probe using the pneumatic air lift of the spectrometer system (typically 20 s) were not taken into account. While it is possible that singlet-state lifetimes are longer, the magnetization does not reside in a true singlet state at high magnetic fields. Furthermore, since the OPSY experiment uses large flip-angle pulses, conventional PHIP would lead to the disappearance of the polarized signal after 2-3 such experiments.

Figures 6A, 6B, 6C:
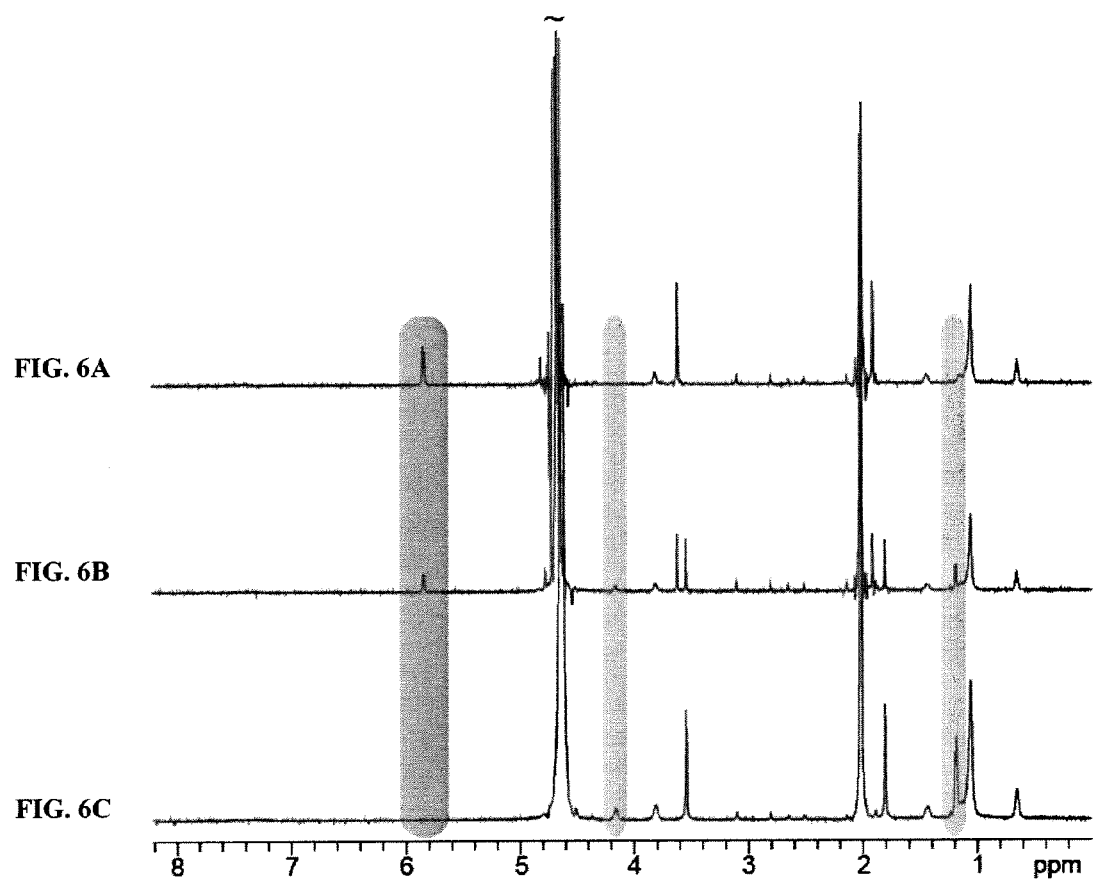
FIG. 6A shows a $^1$H single pulse NMR spectrum at the start of the experiment.
FIG. 6B shows a spectrum after the hyperpolarized signal could not be observed after the first bubbling of p-$H_2$ and series of shakings.
FIG. 6C shows a spectrum after the hyperpolarized signals are not observed from the second bubbling and series of shakes; the peak highlighted in red (5.8 ppm) correspond to the reagent and peaks highlighted in orange (1.2 and 4.7 ppm) correspond to the product.

After bubbling the solution, gaseous partitions were seen along the NMR tube. As the gas flowed through the solution, large gas bubbles were formed due to the presence of SDS. These large bubbles trapped p-H$_2$ in the NMR tube and provided a reservoir of p-H$_2$ without the need of an air-tight seal. Since the p-H$_2$ gas was thus stored in the NMR tube, the reaction could be re-initiated by agitating the solution. Inverting or shaking the NMR tube would release the stored p-H$_2$ gas from the hydrogen storage compartments. This process would dissolve more p-H$_2$ gas into the solution and create small bubbles. As the bubbles rose through the solution they could promote gas diffusion into the bulk solution. After shaking the NMR tube, the hyperpolarized signals appeared again at 1.2 and 4.2 ppm. This step could be repeated for an additional 4 times and the signal lasted for more than 200 s per agitation (FIG. 5A). After several repetitions, shaking the NMR tube did not result in any observable hyperpolarized signal. By measuring the reactant concentrations from the single pulse spectrum (FIGS. 6A and 6B), signals corresponding to the reagent were still present suggesting that the p-$H_2$ supply must have been exhausted. Replenishing the p-$H_2$ gas in the NMR tube by bubbling a second time allowed for the recovery of the hyperpolarized signal (FIG. 5C); after shaking again, the signal lasted for more than 300 seconds (FIG. 5C). The sample was shaken for a total of eight times before the substrate was consumed (FIG. 6C).

In another embodiment for the present invention, higher concentrations of a surfactant can increase the solubility of the substrate in water. Several surfactant concentrations have been explored (Table 1).

TABLE 1

Experimental Ratios and Weights of Methyl 2-Acetamidoacrylate and SDS.

| Reagents | MW (g/mol) | WEIGHT (g) | Moles ($\times 10^{-6}$) | RATIO | Mole % |
|---|---|---|---|---|---|
| Methyl 2-acetamidoacrylate | 143.17 | 0.0033 | 23.0 | 1 | 4.7% |
| SDS | 288.38 | 0.0003 | 1.07 | 0.046 | |
| Methyl 2-acetamidoacrylate | 143.17 | 0.0037 | 25.8 | 1 | 9.4% |
| SDS | 288.38 | 0.0007 | 2.42 | 0.094 | |
| Methyl 2-acetamidoacrylate | 143.17 | 0.0035 | 24.4 | 1 | 19.9% |
| SDS | 288.38 | 0.0014 | 4.85 | 0.199 | |
| Methyl 2-acetamidoacrylate | 143.17 | 0.0037 | 25.8 | 1 | 30.9% |
| SDS | 288.38 | 0.0023 | 7.97 | 0.309 | |
| Methyl 2-acetamidoacrylate | 143.17 | 0.0029 | 20.5 | 1 | 62.6% |
| SDS | 288.38 | 0.0037 | 12.8 | 0.626 | |
| Methyl 2-acetamidoacrylate | 143.17 | 0.0037 | 25.8 | 1 | 73.9% |
| SDS | 288.38 | 0.0055 | 19.0 | 0.739 | |

Figure 8:
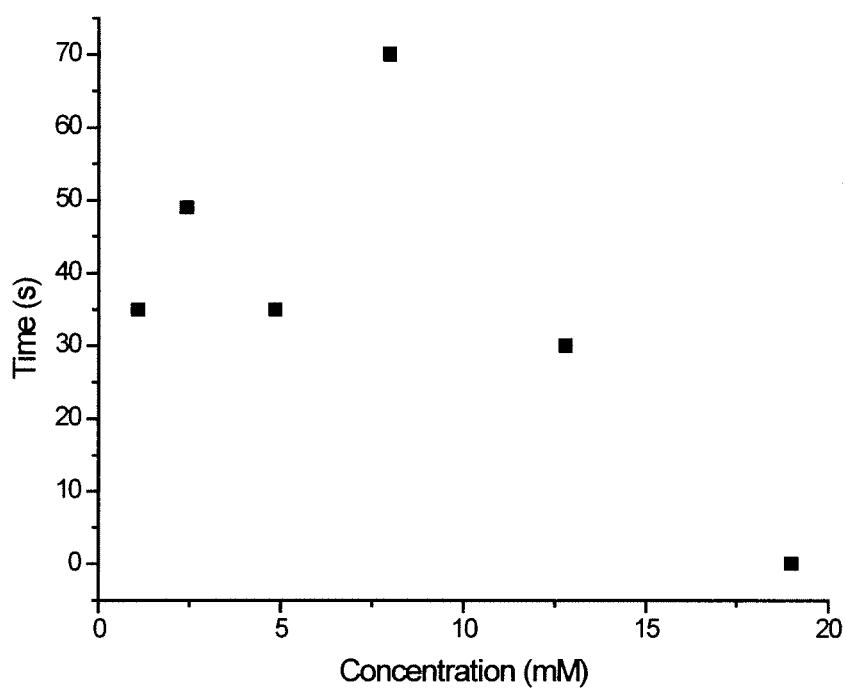
FIG. 8 shows a plot of signal lifetime for the hyperpolarized peaks for the peak at 1.2 ppm as a function of SDS concentration after the initial bubbling of the solution with p-$H_2$.

As the concentration increased two observations were made. First, the signal intensity increased and second, the lifetime of the observable signal becomes longer. Increasing the surfactant concentration to $7.97 \times 10^{-3}$ M, the signal lifetime more than doubled with respect to the sample where the concentration was $1.07 \times 10^{3}$ M and $2.42 \times 10^{-3}$ M. Above $7.97 \times 10^{-3}$ M, the lifetime was reduced to nearly 30 s. (FIGS. 7A, 7B and 8). Not only SDS but also a cationic surfactant (hexadecyltriethylammonium bromide) were observed to produce similar effects.

Kinetics Experiments.

Wietbrecht et al. have shown that the rate of the reaction was independent of the substrate concentration in a similar system. They attributed the zero-order reaction rate to the stabilization of the catalyst complex. Kinetic order was examined in the reaction. Different catalyst concentrations were also examined in order to test its influence on the kinetics of the reaction in a 25:75 MeOD:$D_2O$ mixture (Table 2).

TABLE 2

Catalyst concentrations used in preparing the solution containing $10.4 \times 10^{-3}$M SDS and $20.9 \times 10^{-3}$M of the substrate in 25:75 MeOD:$D_2O$.

| Catalyst Concentration (M) | % ratio w.r.t. [substrate] |
|---|---|
| $0.11 \times 10^{-3}$ | 0.5 |
| $0.21 \times 10^{-3}$ | 1.0 |
| $0.53 \times 10^{-3}$ | 2.5 |
| $1.05 \times 10^{-3}$ | 5.0 |
| $2.10 \times 10^{-3}$ | 10 |

Figure 9:
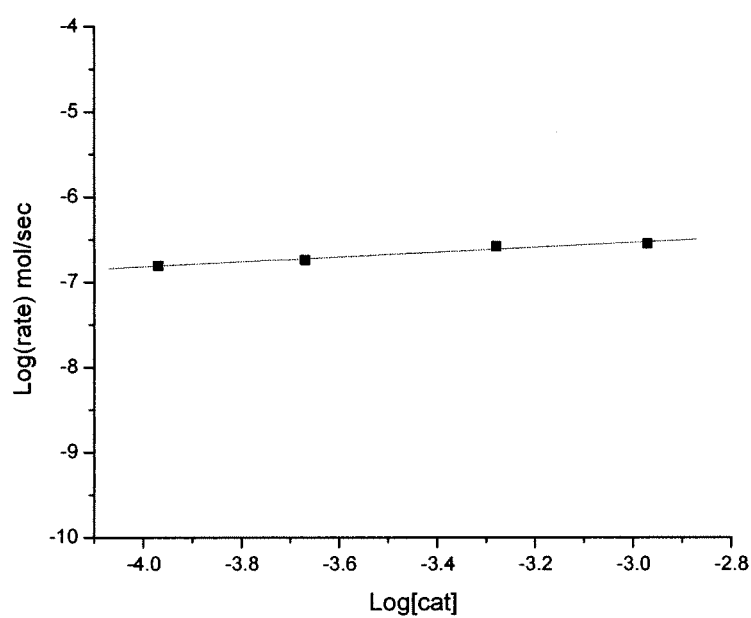
FIG. 9 shows a plot of log(rate) over log [cat] showing a zero order kinetics.
Figure 10:
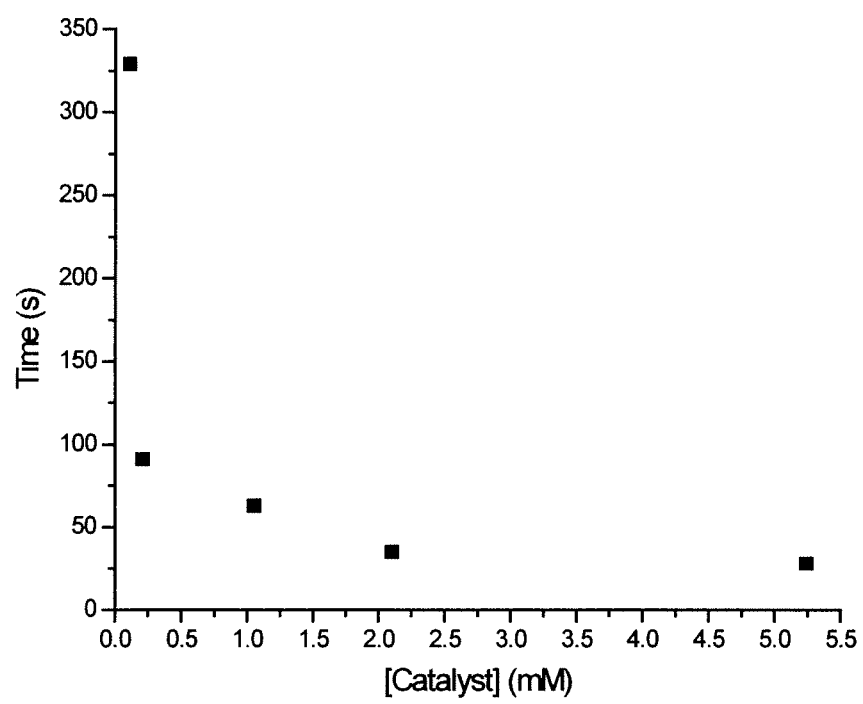
FIG. 10 shows a plot of signal lifetime as a function of catalyst concentrations. Times were measured after second filling of the NMR tube with p-$H_2$ gas.

To ensure that a minimal amount of sample is lost when adding the p-$H_2$ gas, experiments were done using an NMR tube with a Young valve and the gas was pressurized in the tube. Substrate concentration was maintained constant at $21 \times 10^{-3}$ M for all experiments as well as SDS concentration at $10.4 \times 10^{-3}$ M. While increasing the amount of catalyst used in a reaction, the amount of product produced should vary linearly with the catalyst concentration. With $0.11 \times 10^{-3}$ M catalyst, 6.43% of the reagent was hydrogenated to methyl 2-acetamidopropanoate. Doubling the concentration to $0.21 \times 10^{-3}$ M only 2.6% of product was produced. The product yield was 8.6% when using $1.05 \times 10^{-3}$ M of catalyst. By further increasing the catalyst concentration to $2.1 \times 10^{-3}$ M, the amount of product was lower with only 1.2% of the reagent being reacted. The small variation in product yield when changing the catalyst concentration indicates that the $H_2$ gas availability in the solution could be the limiting step in the reaction (FIG. 9). The lifetime of the hyperpolarized signal followed an exponential trend as the catalyst concentration increased. The signal was observable for more than 300 s when using a catalyst concentration of $0.11 \times 10^{-3}$ M. Doubling the concentration, the lifetime reduced by more than a factor of 3. Further increasing the concentration to $2.1 \times 10^{-3}$ M the lifetime of the signal reduced to 28 s (FIG. 10).

Clear evidence is presented for a continuous supply of p-$H_2$ to the hydrogenation reaction in an NMR tube. Repeated application of the OPSY experiment would destroy any hyperpolarized signal at a rate of at least $2^N$, where N is the number of repetitions. Hyperpolarized signals are shown to persist over a number N larger than 10, however, and over 35 times longer than $T_1$ (which were measured to be 5.2 and 7.7 s). These results indicate that new product is being continuously formed. Calculations further indicate that after repeated shaking or bubbling, the reaction proceeds to completion. $H_2$ gas is supplied in an excess to the NMR tube (5 mL compressed-$2.2 \times 10^4$ mol), while the substrate content is typically $2.09 \times 10^{-5}$ mol. After one sample agitation period the typical yield is 5.4%, which would correspond to a $H_2$ consumption of $1.13 \times 10^{-6}$ mol. This yield could also be achieved by consuming $H_2$ dissolved in the reaction mixture, if diffusion of $H_2$ to the reaction center can be considered being the rate limiting step. In 100% water, the solubility of $H_2$ is $7.8 \times 10^{-5}$ M and in 100% methanol the solubility would be $4 \times 10^{-3}$ M. In the 25% MeOH/$H_2O$ mixture used here, therefore it may be estimated to have a solubility of approximately $1 \times 10^{-3}$ M $H_2$ gas, amounting to $1 \times 10^{-6}$ moles in the reaction mixture (assuming 1 mL volume), which is approximately equal to the yield. On the other hand, long lifetimes were also seen for experiments with 100% water solution and SDS. It is possible that SDS promotes dissolution of $H_2$. This shows that the surfactant concentration is crucial in solubilizing $H_2$ gas and reducing the bottleneck in its transport to the reaction centers. One can imagine this happening by means of reducing the surface tension, thereby providing larger surface area, and by creating hydrophobic micro-environments in the form of micelles.

The experiments indicate that the continuous supply of p-H$_2$ for hyperpolarization is due to small storage compartments within the solution. This circumstance is observable in the present study as a result of the lack of dependence of the reaction rate on catalyst concentrations under the reaction conditions, resulting in the reaction rate responding only to H$_2$ availability. The observed reaction is therefore highly sensitive to the factors affecting hydrogen transport in solution.

In some embodiments of the invention, adjusting the surfactant concentration helps prolong the hyperpolarized signal. The lifetime increases as the SDS concentration increases up to 7.97×10$^{-3}$ M. Above this concentration, the signal lifetime decreased. The prolonged existence of the signal could be related to tiny bubble formation. As the concentration of the surfactant increases, smaller bubble sizes can be produced. Above the critical micelle concentration (CMC) the bubbles could be as small as 77 μM to 150 μM. The presence of bubbles aids in the diffusion of gas into solution, on the one hand, and provides a reservoir from which hydrogen gas is supplied to the reaction continuously. Based on the Young-Laplace equation, when the bubble size decreases, the internal pressure increases thus promoting gas diffusion into the surrounding solution.

Figure 11:
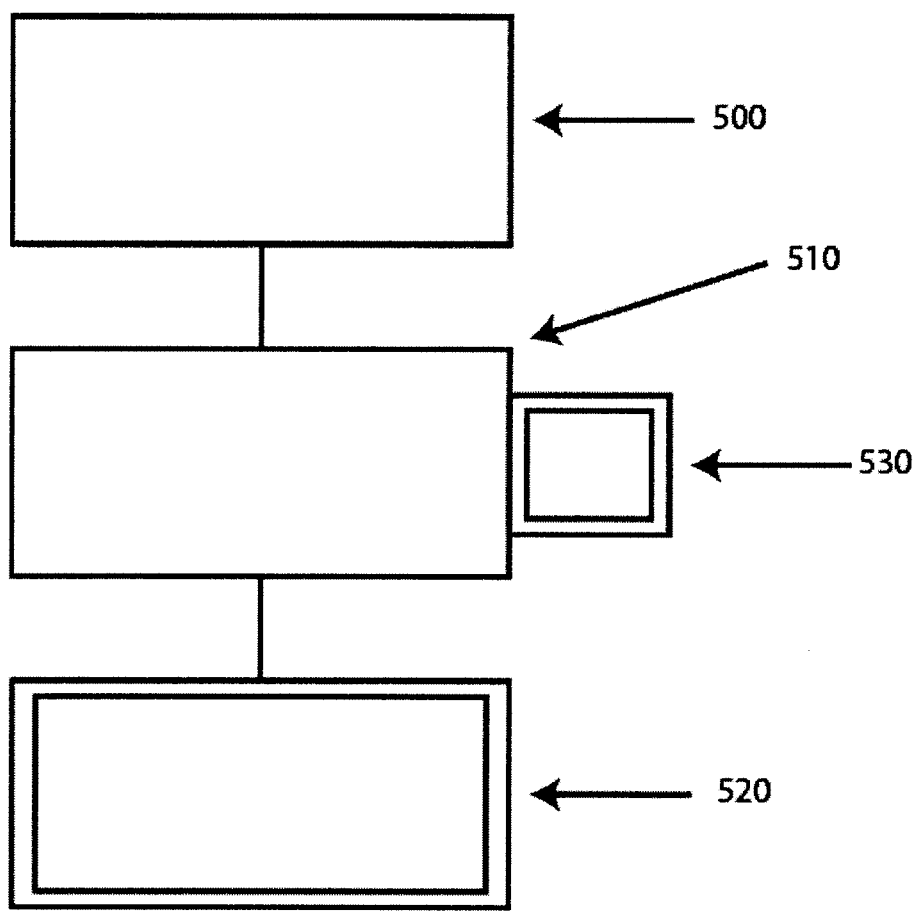
FIG. 11 shows a schematic block diagram of a computer based system for analysis of data and display of information.

In order to implement the NMR spectroscopy system and MRI methods, the preferred form of the invention is implemented by us of a computer based system 500 shown in FIG. 11. In particular, an NMR or MRI form of the system 500 may be controlled by a hardware processing arrangement (aka hardware processor or computing device) 510 and may be connected to an output display 520 as well as a storage medium 530 (aka hardware storage, physical memory, etc) which may contain instructions in the form of computer software or other executable hardware system which may be executed by the processing arrangement 510. The processing arrangement may control the MRI instrument 500 and also obtain the resultant information from a sample according to the present invention. The processing arrangement 510 may also be used to calculate images, which may then be displayed on output display 520 or may be stored in storage medium 530.

This method and system enables the establishment of polarization-enhanced signals which persist for times much longer than T$_1$. The origin of these signals can be traced at least in part to the substantially continuous supply of hydrogen to the reaction. The mechanism preferably includes the appearance of "microstorage" of hydrogen gas within the solution rather than being simply due to increased gas solubility. The use of p-H$_2$ provides a convenient way for identifying this process, as it would be extremely difficult to measure the reaction progress by using thermally polarized hydrogen. Using suitable modifications, the technique can be used for at least the following applications:

Enhancing the availability of hyperpolarized contrast agents in solution, in situ, or in vivo.
Providing H$_2$ storage in solution (H$_2$ gas could be delivered in a solution).
Applications of this methodology could range from catalysis to the study of reaction mechanisms.
Studying macromolecule and protein structure and dynamics.
Enhanced detection of peptides and proteins and the study of their structures and dynamics.
Enhanced and persistent polarization transfer from other gasses, such as Helium, Xenon, Fluorine, Deuterium, Oxygen, or other species such as para-H$_2$O, which have been polarized via different polarization enhancement methods including the distinction between ortho and para species, optical pumping, or by magnetization transfer from radicals.

One particular application of this technology for imaging in humans. The application in humans could involve surfactant; but also other microvesicle platforms, such as liposomes. Thus, stable vesicles can be created that carry p-H$_2$ to a target site where the hydrogenation reaction may occur in situ to produce hyperpolarized molecules that would act as tracers for MRI imaging, or that could be further metabolized to reveal biochemical processes by NMR spectroscopy. The liposome could also deliver that pre-hydrogenation precursor and catalyst, or these could arrive at a targeted site by other means. This technology would solve the current problem with p-H$_2$ imaging approaches, that is, the very short lifetime of hyperpolarized species arising from p-H$_2$.

The following non-limiting Examples illustrate experimental conditions used in some of the analyses carried out for the method, system and formation of an article of manufacture for the invention.

Example 1

Reagents

All solid and liquid compounds were purchased from Sigma-Aldrich except for (−)-2,2-dimethyl-4,5-bis(diphenylphosphino)methyl-1,3-dioxolane ((−)DIOP) which was purchased from Alfa Aesar. All compounds were used without further purification.

Catalyst Preparation:
0.625 mg (1.25×10$^{-6}$ mol) of (+2,2-dimethyl-4,5-bis(diphenylphosphino)methyl-1,3-dioxolane ((−)DIOP) was added to a solution of 0.425 mg (1.04×10$^{-6}$ mol) of bis(1,5-cyclooctadiene)rhodium(I)tetrafluoroborate in 0.25 mL of pre-degassed H$_2$O and 0.25 mL of pre-degassed MeOH. The solution was stirred under Argon for 30 minutes at room temperature.

Hydrogenation in NMR Tube:
Methyl 2-acetamidoacrylate and SDS were dissolved in 0.5 mL of pre-degassed D$_2$O. Various concentrations of the reagent and surfactant were utilized as described in Table 1. In a septum screw capped NMR tube, 0.5 mL of the reagent mixture was added to the NMR tube. 0.5 mL of the catalyst was added using a syringe and the solution was bubbled with p-H$_2$ gas.

NMR Spectroscopy:
All experiments were conducted on an 11.74 T ($v_0$($^1$H)=499.859 MHz) Bruker Avance NMR spectrometer equipped with a multinuclear broadband inverse (BBI) liquids probe. $^1$H NMR spectra acquired using a single-pulse experiment employed a π/2 pulse width of 5.3 μs and a recycle delay of 2.0 s. One transient was collected for each spectrum. For the p-H$_2$ enhanced $^1$H NMR experiments, the Only Parahydrogen SpectroscopY (OPSY) sequence was employed. The gradient strengths for the first and second gradients were 6.25 and 12.5 G/cm both for a duration of 1.2 ms. A single transient was collected for each spectrum.

Additional Experimental Details:
The conversion of hydrogen gas to p-H$_2$ was done using an in-house built portable parahydrogen apparatus. For the conversion from ortho- to parahydrogen, a copper tube containing activated charcoal catalyst was submerged in liquid nitrogen for approximately 15 min. The initial H$_2$ gas within the apparatus is purged before introducing p-H$_2$ to the sample at a low magnetic field, approximately 3 m away from the NMR magnet, and at ambient temperature and pressure. The gas was inserted into the solution in one of two ways: (i) the p-$H_2$ gas was bubbled through the septum of the NMR tube for 15 seconds (to relieve pressure in the tube, the cap was loosely screwed onto the NMR tube) and (ii) the NMR tube (equipped with a Young valve) was pressurized by adding 5 mL of p-$H_2$ gas to the headspace of the tube. The tube was then agitated (by shaking and/or inverting) for 20 seconds.

The sample was then placed at the top of the magnet and transported to the probe using the pneumatic air lift of the Bruker NMR system. The typical time required for the sample to go down the bore of the probe was measured as 11 s. Once a signal lock was established, the experiment was initiated. Sequential spectra were acquired in a 2-dimensional manner with a 7 second delay between each experiment unless otherwise stated.

After the hyperpolarized signal completely decayed, the sample was removed and "shaken"; the tube was inverted two times and vigorously shaken twice. The sample was placed back at the top of the magnet bore and brought back down to the probe. A new experiment was executed as soon as the signal lock was achieved. The total time from the start of adding p-$H_2$ to the solution to the establishment of the lock was approximately 40 s. This time includes bubbling/shaking (15/25 sec), walking over to the spectrometer and placing at the top of the bore (~10 s), bringing it down with the airlift (11 s) and getting a lock (3 s).

Example 2

Thiostrepton (FIG. 12) is a natural occurring antibiotic from Streptomyces azureus and was only completely biosynthesized recently. Thiostrepton possesses four potential amino acid residues in which hydrogenation can occur: three dehydroalanine (Deala) and one methylbutyl (But) group. It has been widely studied due to unique features, biosynthesis and newly discovered anticancer properties. Example 2 and Example 3 focus on the effect of hyperpolarization to enhance and isolate specific sites in a peptide was studied.

Reagents.

All solid and liquid compounds were purchased from Sigma-Aldrich except for (−/+)-2,2-dimethyl-4,5-bis(diphenylphosphino)methyl-1,3-dioxolane ((−/+)-DIOP) which was purchased from Alfa Aesar. All compounds were used without further purification.

Catalyst Preparation.

The quantity 0.62 mg ($1.25 \times 10^{-6}$ mol) of (−/+)-2,2-dimethyl-4,5-bis(diphenylphosphino)methyl-1,3-dioxolane ((−/+)DIOP) was added to a solution of 0.42 mg ($1.04 \times 10^{-6}$ mol) of bis(1,5-cyclooctadiene)rhodium(I)tetrafluoroborate in 0.5 mL of pre-degassed $CDCl_3$/MeOD 4:1 mixture. The solution was stirred under argon for 30 minutes at room temperature.

NMR Spectroscopy.

All NMR experiments were performed using a Bruker Avance Spectrometer operating at 11.74 T ($v_0(^1H)$=499.859 MHz). When acquiring spectra with hyperpolarized signals, a single pulse experiment was performed using a 45° flip angle. The OPSY sequence was employed to suppress thermal signals. All experiments were obtained with a single acquisition. Spectra from the single pulse experiment were processed by phasing the thermal peaks and the OPSY spectra were unphased.

Figures 13A, 13B, 13C:
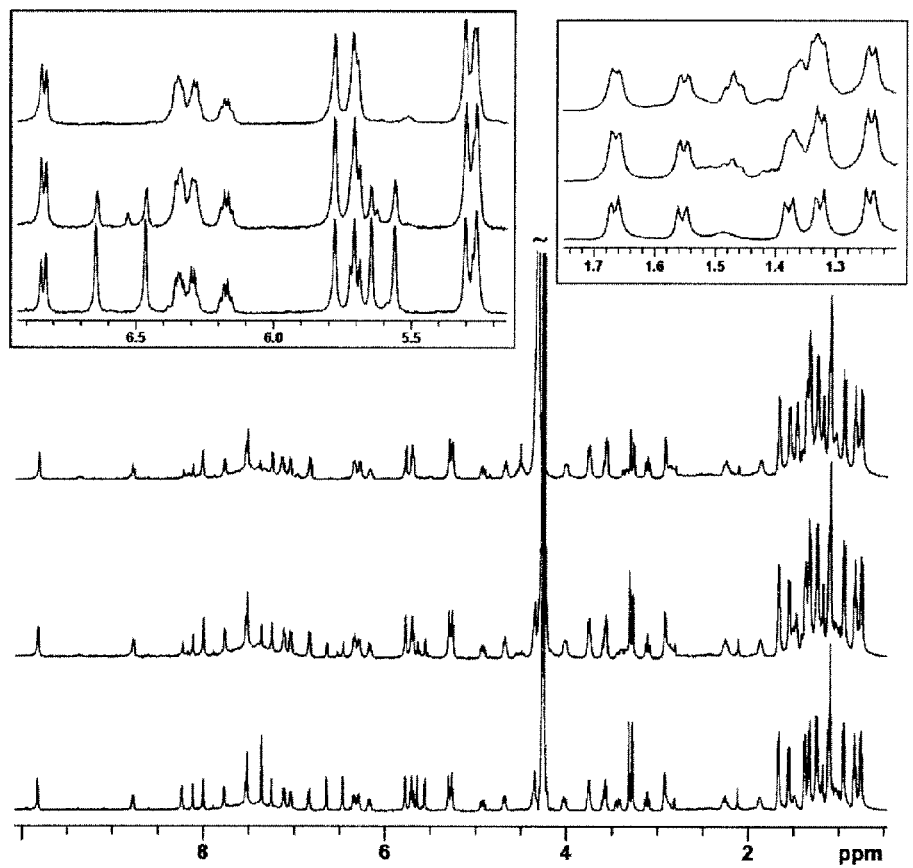
FIGS. 13A-C shows a $^1$H NMR spectra of thiostrepton showing the reagent peaks at the start (13A), after bubbling for 30 s (13B), and after complete hydrogenation (13C) with the spectra inset focus on $CH_2$ peaks of Dealanine and $CH_3$ peaks of the Alanine residues (indicates the strong solvent peak).

Hydrogenation/Hyperpolarization.

p-$H_2$ was generated by flowing $H_2$ gas through activated charcoal at 77K. The sample was bubbled for 30 seconds at low magnetic field then inserted into the probe using the automated air lift of the Bruker system. Once a lock was established the experiment was executed. Total time from the start of the bubbling to the start of the experiment was approximately 50 seconds. There is evidence of the Deala(2) and Deala(3) being the primary amino acid residues being hydrogenated based on the single pulse NMR spectra shown in FIG. 13.

The peaks at 5.65/6.64 and 5.56/6.46 ppm, corresponding to the $CH_2$ protons of Deala(2) and Deala(3), respectively which are depleted after hydrogenation. The signals for Deala (1) (5.77/5.30 ppm) and But (6.17/1.55 ppm) are unaffected. Traces of newly developed alanine groups are seen at ca. 4.52 and 1.34 ppm but are hindered by the reagent signals. Producing hyperpolarized peaks for the products show a typical antiphase pattern, however the intensity is not as strong and the interference of the thermal peaks make it difficult to clearly distinguish the different sites (FIG. 14A).

With the OPSY pulse sequence three signals are observed (FIG. 14B). In addition to the expected alanine peaks described above, hyperpolarized signals at 4.68, 4.37, 1.41, and 1.5 ppm are also observed. These peaks may correspond to species that are mono-hydrogenated. At the time of acquisition, it is possible that in addition to complete hydrogenation, only either Deala(2) or Deala(3) or a mixture of both is hydrogenated at one time exhibiting a chemical shift difference from the situation where both are saturated. New peaks emerge at 5.62 and 6.53 ppm after bubbling the solution for 30 s. If only Deala(2) or Deala(3) is hydrogenated then $CH_2$ peak of the other Deala residue would shift since it is now in a different chemical environment. When completely hydrogenated all peaks corresponding to Deala(2) and Deala (3) disappear indicating all of these sites are saturated.

Electrospray mass spectrometry (ESI-MS) also verifies that only two sites are being hydrogenated showing only 4 units being added to the overall molecular mass. The initial spectrum displays a single peak at 1663.7 m/z indicating pure thiostrepton. After stirring the solution under $H_2$ atmosphere until complete hydrogenation, a peak at 1667.6 m/z appears indicating only four hydrogen atoms are added to the overall structure. Distinguishing between the two different diastereomers conformations of the alanine using hyperpolarized signals may prove to be useful in determining chemical properties. To examine the possibility of distinguishing the two diastereoisomeric structures of the alanine groups, the hydrogenations were performed using enantiomeric specific catalysts; (−)-DIOP and (+)-DIOP, $^1H$ OPSY NMR spectra comparing the products of the different catalysts show a shift to a lower field of about 10 Hz when −(−)DIOP was used and a signal about 5 times more intense when (+)-DIOP was used.

Example 3

In-Situ Hydrogenation with Para-$H_2$ para-$H_2$ was generated by flowing $H_2$ gas through activated charcoal at 77K. The gas was then bubbled through the reaction solution in an NMR tube for 15 seconds, after which the tube was inserted into the probe using a string to minimize the sample transfer time. Once lock was established the experiment was executed. Total time from the start of the bubbling to the start of the experiments was approximately 30 seconds.

Signal Enhancement

Compared to the thermal signal, enhancement factors of 56 and 23 are achieved when using the catalyst with (+) and (−) DIOP ligands, respectively. Even though the enhancement factors appear relatively low compared to simple model systems, it should be emphasized that this is expected for a molecule of this size and complexity. The OPSY spectra are rich in information nonetheless, since the para-hydrogenated groups act as spin polarization labels.

Simulations of OPSY Spectra

The simulation of the OPSY spectra was performed in Matlab (r2010a, the Mathworks Inc, Natick, Mass.). The density matrix of each coupled spin pair is evolved through each pulse and free evolution period in the OPSY sequence and a double quantum filter is applied before the readout pulse. For compound 4 (thiostrepton), the chemical shifts used in the simulation are 4.69-1.37 ppm, 4.54-1.54 ppm, 4.51-1.49 ppm, 4.37-1.34 ppm and 4.40-1.42 ppm. For compound 6, δ=4.60-1.48 ppm was used and an additional spin pair at δ=4.71-1.41 ppm was used when assuming there were polarization transfer. All the J-couplings are assumed to be 7 Hz and a $T_2$ of 100 ms is used in all the resonances.

Synthesis

Catalyst Preparation 1 mg (1.95×10$^{-6}$ mol) of (−/+)-2,2-dimethyl-4,5-bis(diphenylphosphino)methyl-1,3-dioxolane ((−/+)DIOP) was added to a solution of 0.7 mg (1.7×10$^{-6}$ mol) of bis(1,5-cyclooctadiene)rhodium(I)tetrafluoroborate in 0.5 mL of pre-degassed CDCl$_3$/MeOD 4:1 mixture. The solution was stirred under Argon for 30 minutes at room temperature. No purification was required.

Synthesis of Compound 2

The synthesis was performed according to literature procedure (H. R. A. Jonker, S. Baumann, A. Wolf, S. Schoof, F. Hiller, K. W. Schulte, K. N. Kirschner, H. Schwalbe, H. D. Arndt, *Angew. Chem. Int. Ed.* 2011, 50, 3308-3312, incorporated herein by reference ("Jonker Literature")). ESI-MS (positive mode) shows peaks at m/z=1596.6 [M+H]$^+$ and m/z=1618.6 [M+Na]$^+$.

Synthesis of Compound 3

The synthesis was performed as described in the Jonker Literature. ESI-MS (positive mode) showed peaks at: m/z: 1526.5 [M+H$^+$] and m/z=1548.5 [M+Na]$^+$.

Synthesis of Compound 4

Figure 15A:
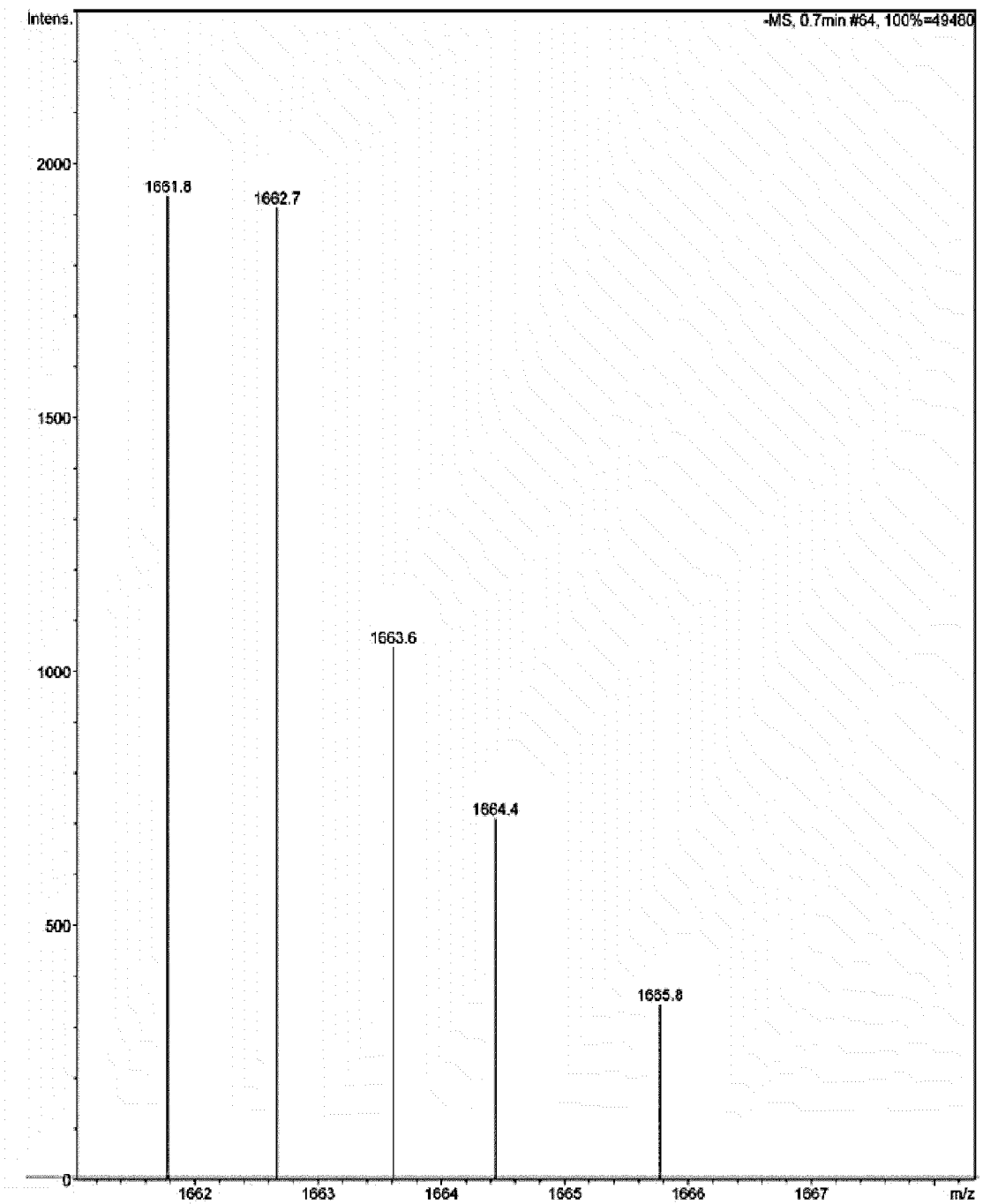
FIGS. 15A-B is a low resolution ESI-mass spectra (negative mode) of (A) thiostrepton, 1 and (B) hydrogenation product, 4.
Figure 15B:
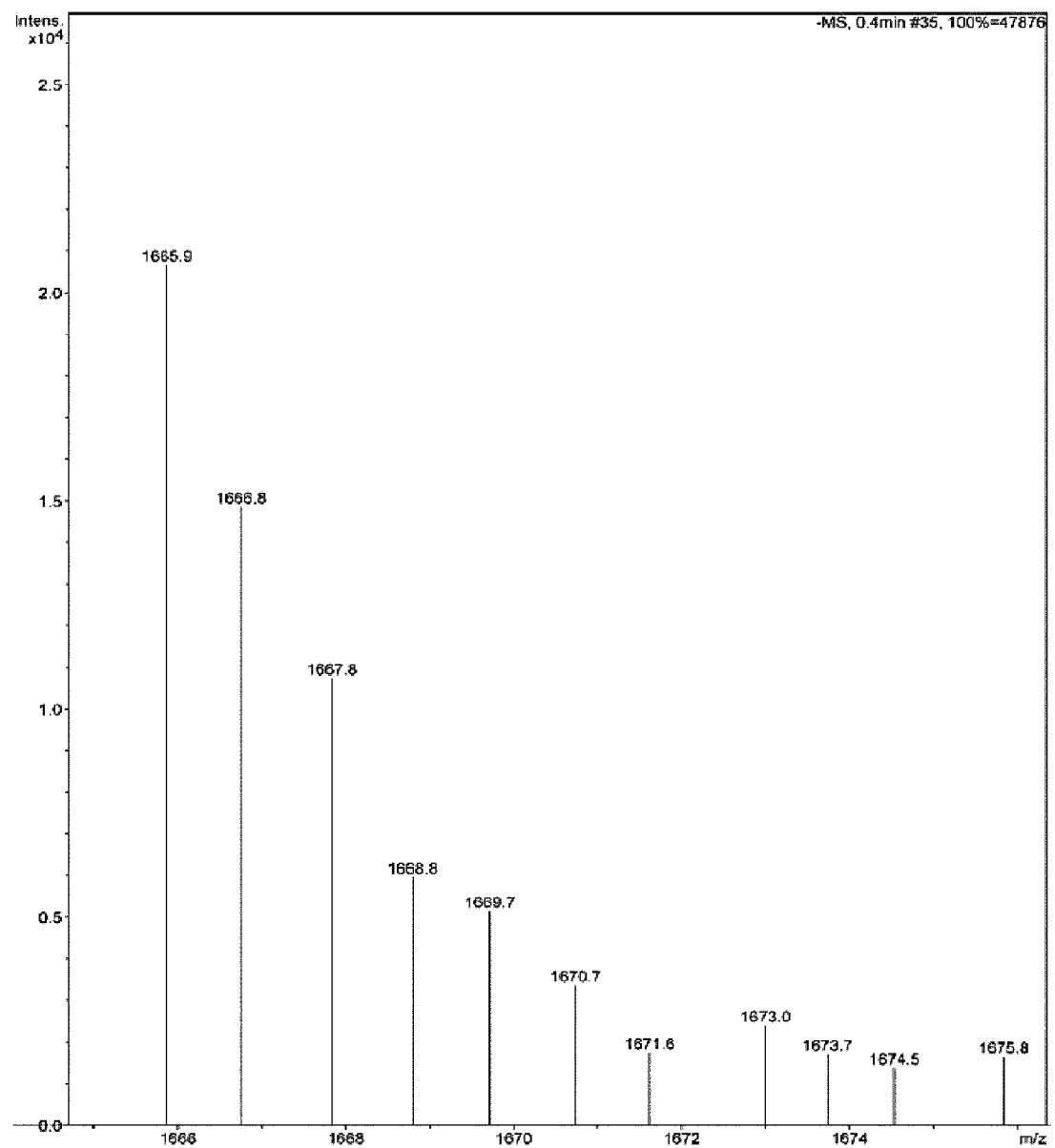

Thiostrepton (10 mg, 6×10$^{-6}$ mol) was dissolved in 0.5 mL of 4:1 mixture CDCl$_3$/MeOD. 1.7×10$^{-6}$ mol of catalyst: (1,5-cyclooctadiene)rhodium(I)((−/+)DIOP) tetrafluoroborate previously prepared were added to the solution and H$_2$ or p-H$_2$ was bubbled into the reaction for 15 seconds at a time, for a total of 1-4 hours, at which time the reaction was determined to be complete. ESI-MS negative mode showed a peak at 1665.9 [M−H]$^-$ (FIG. 15).

$^1$H NMR (400 MHz, CDCl$_3$/CD$_3$OD 4:1) d=9.81 (s, 1H), 8.71 (d, J=8.8, 1H), 8.56 (s, 1H) 8.20 (s, 1H) 8.14 (d, 1H), 8.08 (s, 1H), 7.86 (s, 1H), 7.53 (s, 1H), 7.2 (s, 1H), 7.03-6.99 (m, 2H), 6.80 (d, J=10.0, 1H), 6.30-6.20 (m, 2H), 6.13 (q, J=7.1, 1H), 5.75 (bs, 1H), 5.67-5.57 (m, 2H), 5.25-5.22 (m, 3H), 4.89 (dd, J=8.9, 12.9, 1H), 4.67-4.58 (m, 1H), 4.53-4.47 (q, 1H) 4.35-4.30 (m, 3H), 3.73-3.70 (m, 2H), 3.58-3.53 (m, 2H), 3.07 (dd, J=11.4, 13.0, 1H), 2.83 (d, J=4.3, 1H), 2.78-2.71 (m, 1H), 2.26-2.21 (m, 1H) 2.13 (t, J=12.9, 1H), 1.85-1.80 (m, 1H), 1.64 (d, J=7.8, 3H), 1.53 (d, J=7.2, 3H), 1.44 (d, 7.5, 1H) 1.40-1.36 (m, 1H), 1.35-1.29 (m, 3H), 1.20 (d, J=6.6, 3H), 1.09-1.06 (m, 9H), 0.97 (bs, 1H), 0.91 (d, J=7.7, 1H), 0.80-0.72 (m, 10H)

Synthesis of Compound 6

The procedure used was the same as reported for the synthesis of thiostrepton-H$_4$. $^1$H NMR (400 MHz, CDCl$_3$/CD$_3$OD 4:1) d=9.70 (s, 1H), 8.63 (d, J=8.8, 1H), 8.12 (s, 1H), 8.10 (s, 1H), 8.00 (s, 1H), 7.86 (s, 1H), 7.40 (s, 1H), 7.14 (s, 1H), 6.97 (d, J=7.9, 1H), 6.92 (d, J=7.6, 1H), 6.56 (s, 1H), 6.25-6.15 (m, 2H), 6.15 (q, J=7.1, 1H), 5.77 (d, J=2.1, 1H), 5.70-5.65 (m, 2H), 5.58 (d, J=1.6, 1H), 5.25 (s, 1H), 5.16-5.12 (m, 2H), 4.81 (dd, J=8.9, 4.60-4.52 (m, 1H), 4.28-4.23 (m, 3H), 3.93-3.86 (m, 1H), 3.68-3.60 (m, 2H), 3.51-3.43 (m, 2H), 3.36-3.25 (m, 1H), 3.00 (dd, J=11.4, 13.0, 1H), 2.80 (d, J=4.3, 1H), 2.78-2.71 (m, 1H), 2.13 (t, J=12.9, 1H), 1.79-1.71 (m, 1H), 1.55 (d, J=6.6, 3H), 1.47 (m, J=7.1, 3H), 1.42-1.37 (m, 1H), 1.26 (d, J=6.6, 3H), 1.21 (d, J=6.6, 3H), 1.13 (d, J=6.4, 5H), 1.03-0.97 (m, 8H), 0.95-0.86 (m, 1H), 0.83 (d, J=6.9, 3H), 0.72 (t, J=7.3, 4H), 0.65 (d, J=6.2, 3H).

Characterizations

Two types of characterizations where performed. Electro-Spray Ionization Mass Spectrometry low resolution experiments were performed on Agilent LCMSD Trap XCT mass spectrometer using positive and negative ionization mode (supported by NSF grant CHE-0234863). High resolution experiments were obtained on an Agilent 6224 Accurate-Mass TOF LC/MS system using positive ionization mode.

In addition, NMR Spectroscopy was also performed. All NMR experiments involving para-hydrogen were performed using a Bruker Avance Spectrometer operating at 11.76 T ($v_0$($^1$H)=500.20 MHz). The flip angle was 45° for the single pulse experiment when acquiring spectra with hyperpolarized signals. When the OPSY sequence was employed, the gradient strength was optimized to suppress the thermal peaks. The typical gradient strength used was 8.4 G/cm for 1.2 ms. The OPSY spectra were acquired through the reaction at a 2 s interval. Spectra from the single pulse experiment were processed by phasing the thermal peaks and the OPSY spectra were not phased. Thiostrepton and its hydrogenation products were also characterized with a Bruker Spectrometer at 18.79 T ($v_0$($^1$H)=800.13 MHz) equipped with cryoprobe. Standard single pulse, COSY, ROESY, and $^1$H-$^{13}$C HSQC experiments were performed for spectral assignments.

Analysis of Example 3

Figure 12:
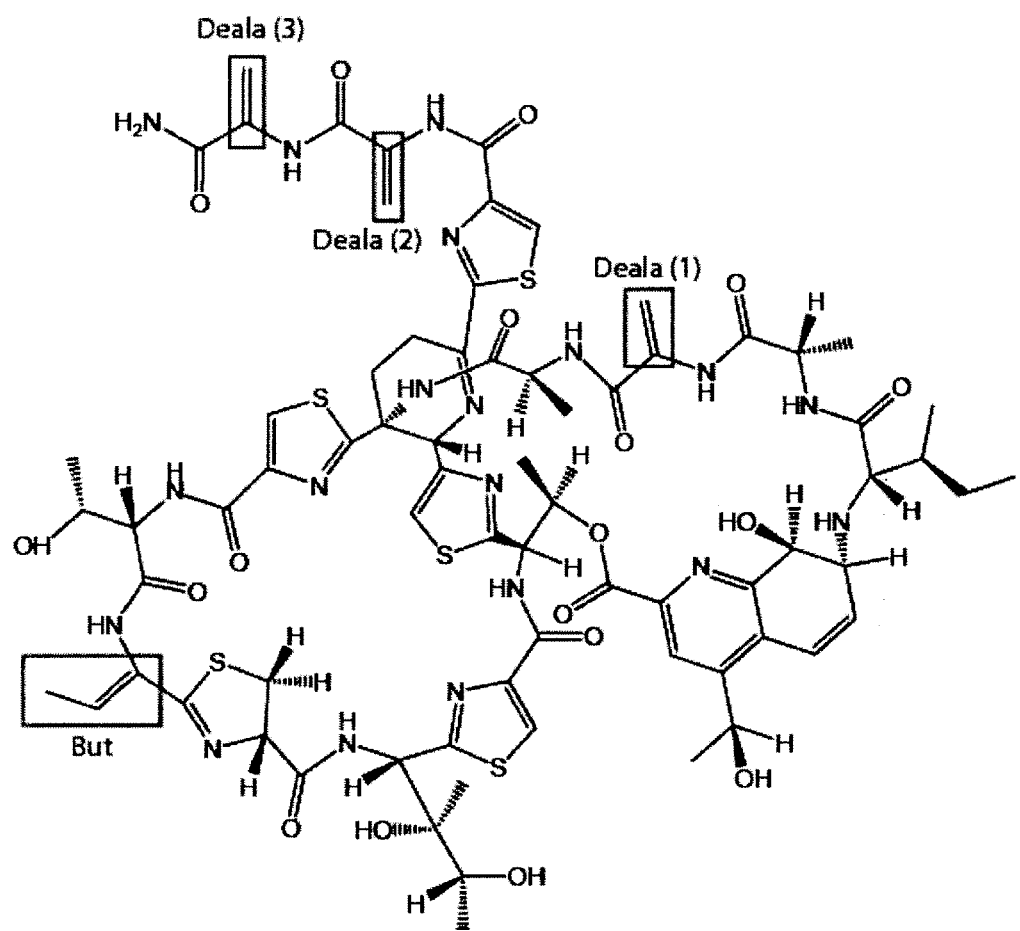
FIG. 12 shows a scheme wherein thiostrepton has four potential sites that could be saturated with hydrogen.
Figure 16:
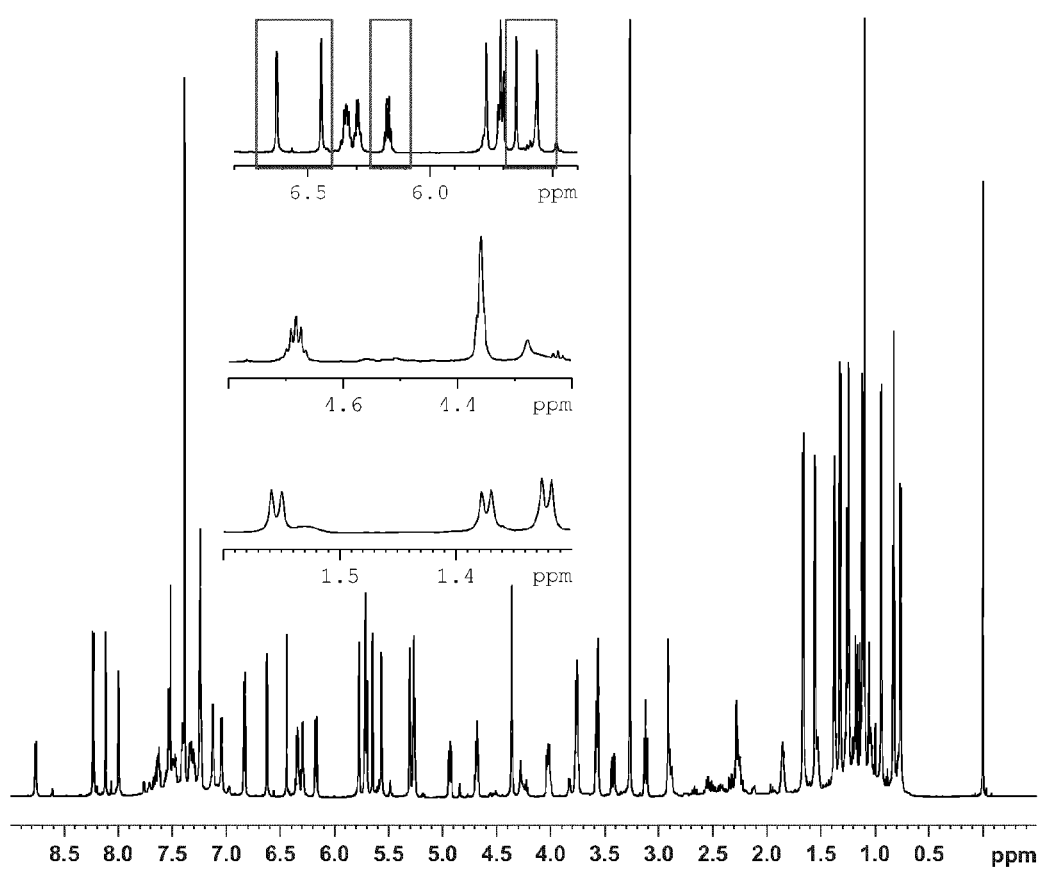
FIG. 16 is a $^1$H NMR spectrum of thiostrepton with catalyst. The peaks at $\delta$=5.65/6.64 and $\delta$=5.56/6.46 ppm, correspond to the $CH_2$ protons of deAla-16 and deAla-17, respectively. The quartet at $\delta$=6.18 ppm corresponds to the CH of dehydro-Butyrine.
Figure 17:
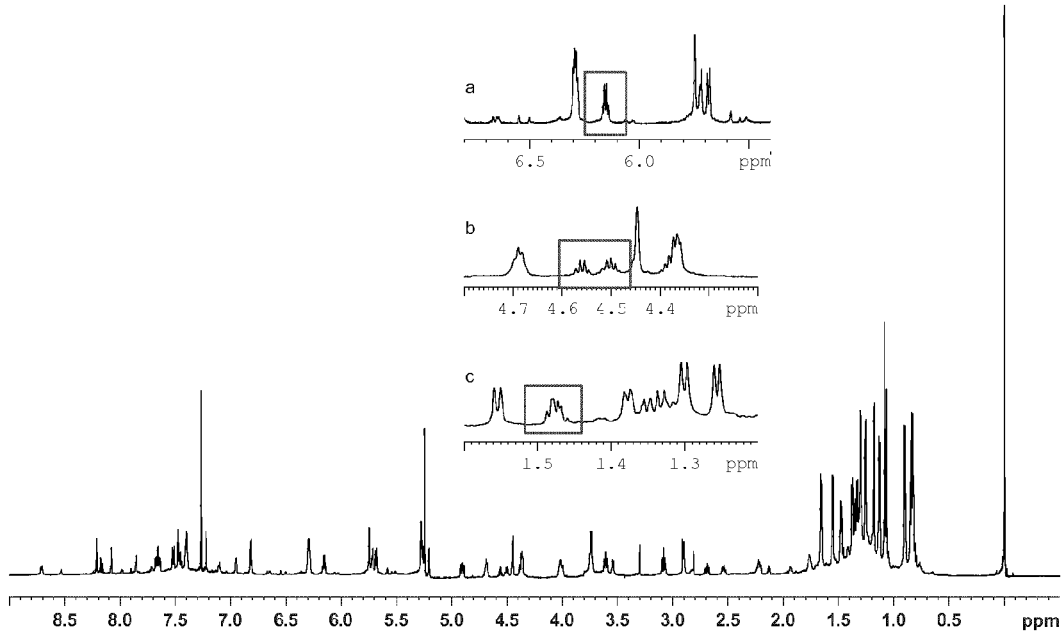
FIG. 17 is a $^1$H NMR spectrum of compound 4. The peaks of deAla-16 and deAla-17 are depleted while the CH in the dehyrobutyrine residue is intact (Inset a). The new peaks in the regions of $\delta$=4.5-4.6 ppm and $\delta$=1.4-1.5 ppm are from the CH and $CH_3$ groups of the newly formed alanines (Insets b and c).
Figure 18:
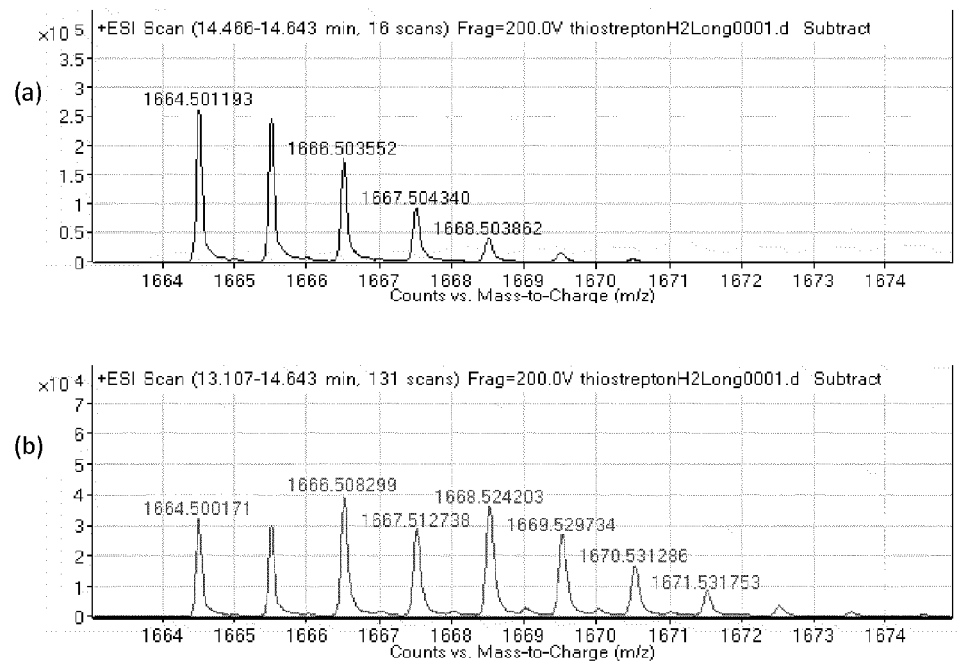
FIGS. 18A-B are a high resolution ESI-MS-TOF spectra (positive mode) of (A) thiostrepton (1) m/z=1664.5 [M+H]$^+$ and (B) partially hydrogenated thiostrepton showing peaks at m/z=1666.5 [M+H$^+$] and 1668.5 [M+H]$^+$ suggesting mono- and di-hydrogenated product (compound 4 and 5a/5b). (Sample was hydrogenated to a similar extent to that observed in the OPSY measurements).

It was found that homogeneous catalysis with [Rh(COD)(DIOP)]BF$_4$ for one hour at room temperature in a 4:1 mixture of CHCl$_3$/MeOH gave a 90% yield of hydrogenated product 4 (Scheme 1) (FIG. 12). Electrospray ionization mass spectrometry (ESI-MS, negative mode) of the product under hydrogenation for 1 hour showed a peak at m/z 1665.9 (M−H$^+$), an increase of mass by four units, compared with thiostrepton (m/z=1661.8), indicating a selective reduction of only two of the double bonds (FIG. 5l). Further addition of hydrogen at longer reaction times was not observed. The $^1$H NMR spectra of the product showed depletion of the peaks at δ=5.56/6.46 ppm and δ=5.65/6.64 ppm, corresponding to the CH$_2$ protons of deAla-16 and deAla-17 (Scheme 1 (FIG. 12), FIG. 16 and FIG. 17), numbering according to linear peptide sequence). The signals for deAla-3 (δ=5.77/5.30 ppm) and But (δ=6.17/1.55 ppm) were unaffected.

Figure 19:
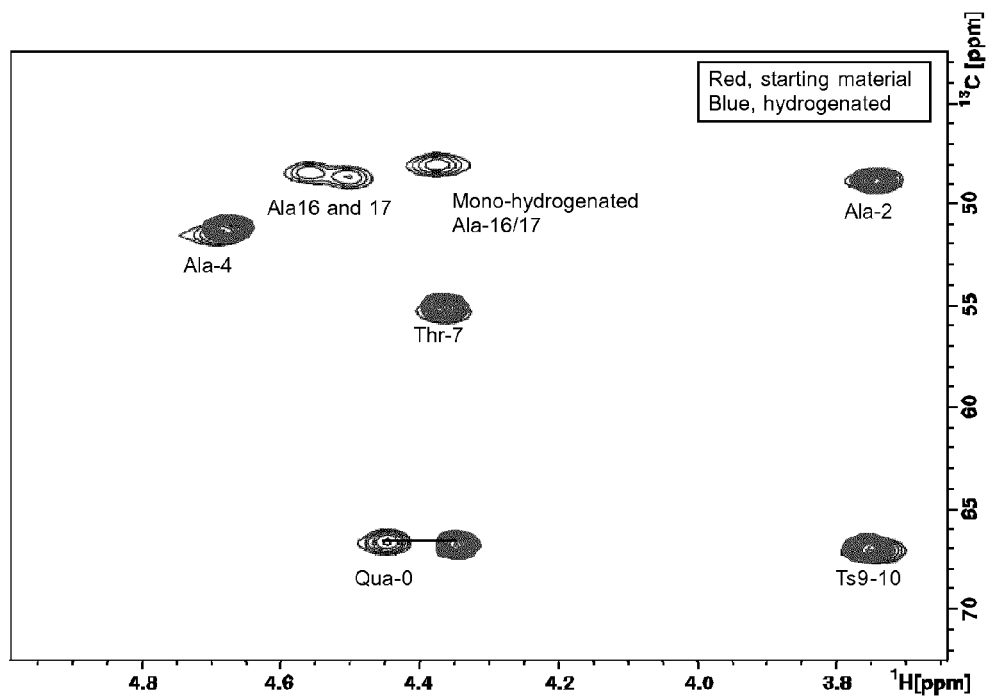
FIG. 19 is a $^1$H-$^{13}$C HSQC spectrum of the thiostrepton starting material, compound 1 (red); and hydrogenated product, compound 4 and 5a/5b (blue).
Figure 20:
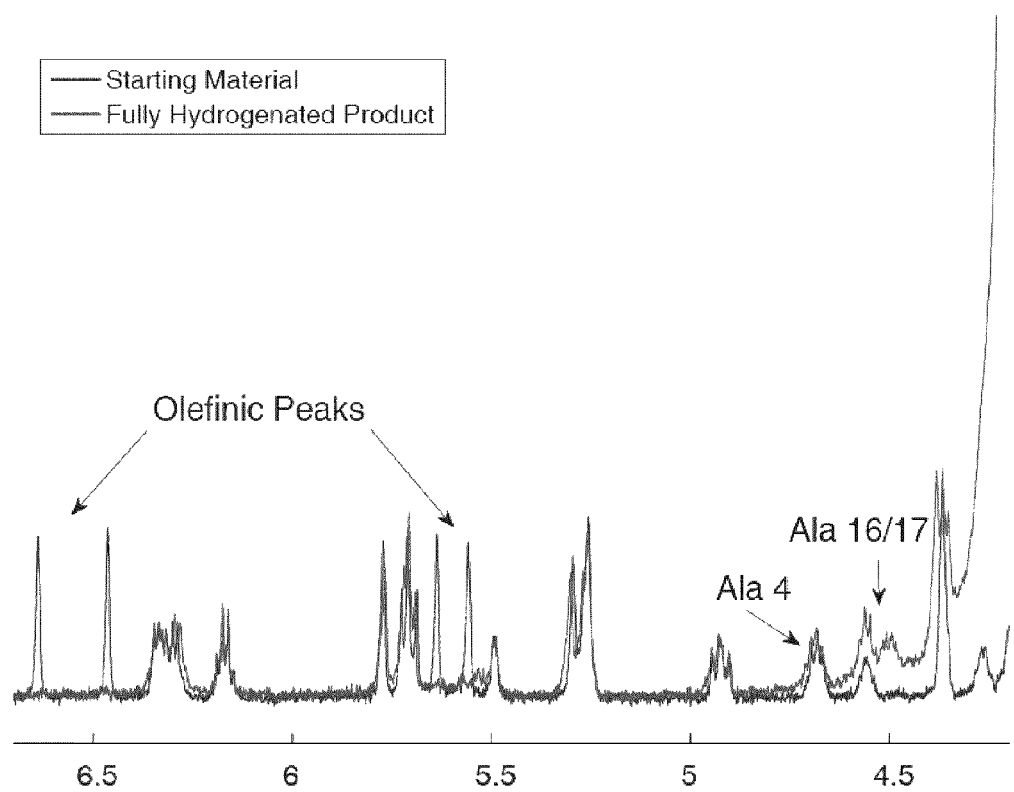
FIG. 20 is a $^1$H NMR partial spectra of thiostrepton (compound 1, blue) and its hydrogenated product (compound 4, red). Neither the chemical shift ($\delta$=4.68 ppm) nor the integration of Ala-4 peak is changed, eliminating the possibility of side reactions at this region.
Figure 21:
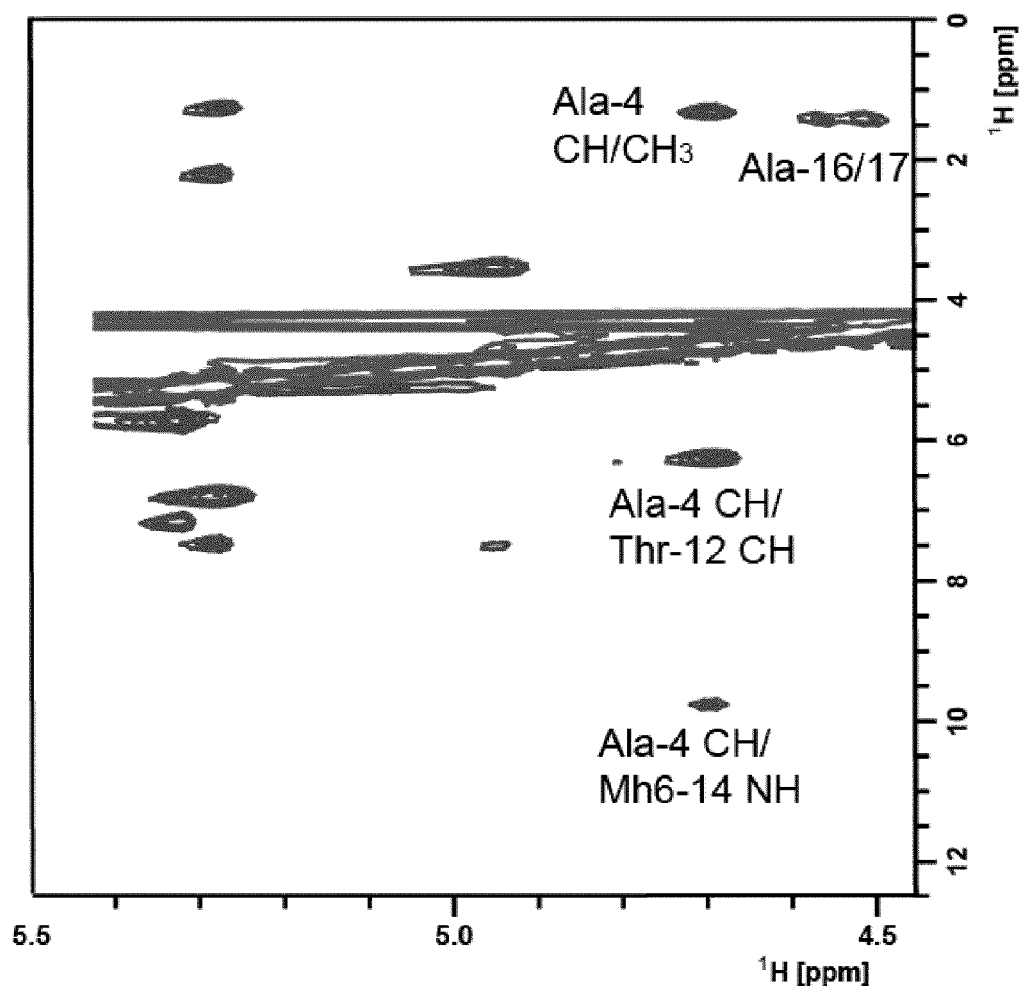
FIG. 21 is a Rotating frame Overhause Effect SpectroscopY ("ROESY") spectrum of compound 4, zoomed in to the methine region. Among the three cross peaks, the peak at $\delta$=4.69/1.37 ppm originates from the correlation between CH and $CH_3$ of Ala-4, and the peak of $\delta$=4.69/9.78 ppm arises from Ala-4 CH and its adjacent NH. The third peak, at $\delta$=4.69/
Figure 24:
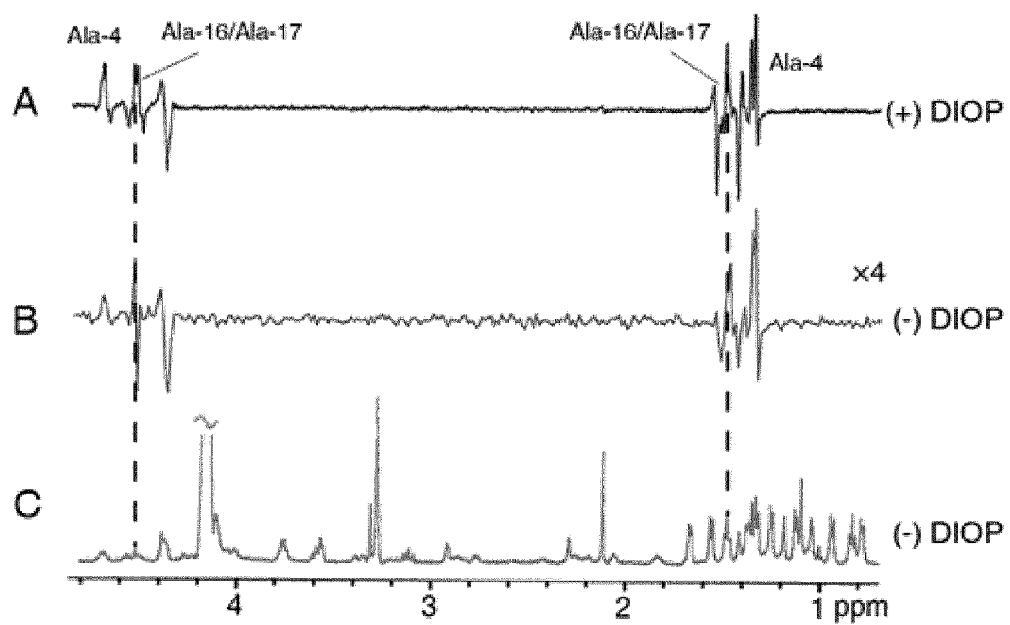

PHIP was used to monitor the reaction in combination with OPSY, which suppresses thermal peaks and isolates only hyperpolarized ones. The $^1$H OPSY spectra observed by hydrogenation of thiostrepton are shown in FIG. 24. Resonances at δ=4.5-4.6 ppm and δ=1.4-1.5 ppm correspond to hydrogenated Ala-16 and 17 in 4. At δ=4.33-4.40 ppm and δ=1.33-1.41 ppm these resonances correspond to products with addition of one equivalent of $H_2$ (i.e., product 5a with Ala-16/deAla-17 or 5b with deAla-16/Ala-17), the formation of which has been confirmed by high resolution ESI-MS-TOF spectrometry and with $^1H$-$^{13}C$ HSQC NMR experiments with samples examined at comparable states of hydrogenation (FIGS. 15 and 19). Surprisingly, additional hyperpolarized peaks were observed at δ=4.69 and 1.37 ppm which correspond to Ala-4 protons according to assignments via 1D and 2D NMR spectra and literature values (FIGS. 19, 20 and 21). The OPSY spectrum was simulated using chemical shifts and J-couplings from both literature values and 2D data and it agrees well with the experimental results (FIG. 25A). Interestingly, however, the Ala-4 group does not possess any unsaturated bonds and hence cannot give a hyperpolarized signal in the OPSY spectrum from simple PHIP, and the signal must therefore derive from polarization transfer.

In an effort to determine the role of the newly formed alanine residues in providing polarization to the Ala-4 residue, compound 3 was synthesized, which does not possess any deAla residues in the tail. The PHIP reaction with this compound did not show any signal in the OPSY spectrum. From this it can be concluded that the polarization transfer to Ala-4 could arise either from an inteiuiediate transfer during the hydrogenation of deAla-16 and deAla-17, or from a through-space transfer after the hydrogenation. This conclusion is reinforced by the fact that attempting the PHIP experiment with 4 under the same conditions did not produce any polarization enhancement. Therefore, a plain SABRE-type non-hydrogenation mechanism for Ala-4 can be ruled out.

Anti-phased signals at the Ala-4 frequency are continuously observed in sequential OPSY experiments, indicating that the hydrogenation reaction continued at high magnetic field, hence the PASADENA mechanism applies here. At high field, the isotropic mixing effect, which is required for an efficient through-bond transfer, is extremely unlikely. Therefore, an NOE-type through-space transfer appears to be the more plausible explanation.

Both mechanisms require a relatively short distance between Ala-4 and the hyperpolarized spins in the tail region. $^1H$ NMR results suggest that the dehydroalanine tail is oriented away from the main body of the molecule, although it is also proposed that the tail is very flexible. Indeed, examination of molecular models indicates that rotations about the C—C and C—N sigma bonds within the deAla-16 and deAla-17 residues bring the deAla-17 and Ala-4 residues within approximately 3 Å of each other (FIG. 22) which may allow such a polarization transfer to occur.

To test which newly formed Ala residue (Ala-16 or Ala-17) is responsible for the polarization transfer, compound 2 was synthesized. Possessing only deAla-16, models indicate that the shorter tail of compound 2 does not have enough flexibility to achieve proximity to Ala-4. FIG. 25B shows the OPSY spectrum from the hydrogenation reaction of 2 (forming 6, black solid line) together with a simulated spectrum (green line), assuming hyperpolarization of both Ala-16 and Ala-4. The experimental spectrum, however, shows only the newly formed Ala-16 signals. As is clearly seen, no transfer has occurred in compound 6, which leaves the deAla-17 derived alanine as responsible for the polarization transfer in the case of thiostrepton.

An examination of the ROESY spectrum of the hydrogenated thiostrepton finds no cross peak between Ala-4 and Ala-16/Ala-17 (FIG. 21), indicating that the conformational change which brings the tail of thiostrepton close to Ala-4 must happen during the hydrogenation process in an intermediate state with the catalyst. It can therefore be concluded that the polarization transfer seen here is the result of a conformational change during hydrogenation, facilitating an efficient NOE-type transfer mechanism. Computational predictions and NMR structures show that the dehydroalanine tail is flexible, a factor thought to be important for proper binding to the target receptor.

The determination of enantioselectivity in peptides is very challenging; although differentiation between diastereomers of peptides by NMR spectroscopy has been performed for peptides possessing as many as 18 amino acid residues, it is a non-trivial task. Bargon et al. (A. Harthun, J. Barkemeyer, R. Selke, J. Bargon, *Tetrahedron Lett.* 1995, 36, 7423) determined the stereoselectivity of a mixture of unsaturated racemic alcohols with Rh(I) metal complexes with p-hydrogenation. Hydrogenation was performed using the two enantiomeric catalysts [Rh(COD)(+/−DIOP)]$BF_4$. The $^1H$ OPSY NMR sequence used for the analysis of the reaction showed that the peaks appearing from the newly formed alanines show 7-10 Hz difference in chemical shifts for both the CH and $CH_3$ peaks (FIG. 24). The ROESY spectra also indicate that the two products have different structures in the tail region. Due to the complexity of the spectrum of thiostrepton, the reaction was further examined with derivative 2. $^1H$ NMR spectra of 6 using the two enantiomeric DIOP ligands are shown in FIG. 26. The methyl peak at δ=1.47 ppm shows clearly that the spectra of the two diastereoisomers partially overlap. The difference in chemical shift of about 7 Hz between the two isomers suggested that the product from (+)DIOP gave a downfield shifted resonance for the methyl substituent, with a diasteriomeric excess of approximately 59%. The (−)DIOP containing catalyst favored the product with upfield shifted methyl group with d.e. of approximately 65%. The methine groups in the δ=4.58 region overlap heavily. OPSY spectra confirmed these results (FIG. 23), showing two sets of methyl groups and only one set of resonances for CH.

Thus, a hydrogenated form of the thiostrepton antibiotic molecule has been analyzed with PHIP. Apart from observing enhanced (and labeled) polarization in the hydrogenated groups, a polarization transfer mechanism to a remote amino acid residue, which is most likely due to a catalyst-mediated through-space transfer, in an intermediate state of the reaction was also identified and verified. Furthermore, the diastereoselectivity of the hydrogenation reaction of this complex molecule was determined. The para-hydrogen labeling and analysis of the present invention ahs been shown to provide for studies with other peptides belonging to the important thiopeptide family to examine structural changes and specific features that would be otherwise undetectable with standard methods.

The foregoing description of embodiments of the present invention have been presented for purposes of illustration and description. It is not intended to be exhaustive or to limit the present invention to the precise form disclosed, and modifications and variations are possible in light of the above teachings or may be acquired from practice of the present invention. The embodiments were chosen and described in order to explain the principles of the present invention and its practical application to enable one skilled in the art to utilize the present invention in various embodiments, and with various modifications, as are suited to the particular use contemplated.

What is claimed is:
1. A method of providing increased longevity of hyperpolarized $^1H$ NMR signals for NMR spectroscopy and magnetic resonance imaging (MRI), comprising the steps of:
 providing a material including a molecular species susceptible of NMR and MRI spectroscopy/imaging;

providing parahydrogen for input to the material; and inputting the parahydrogen to the material by distributing parahydrogen through the material for a time to establish increased longevity of the NMR and MRI signals;

adding a surfactant to the material, thereby providing increased persistence of the parahydrogen for the molecular species.

2. The method as defined in claim 1 further including the step of performing NMR spectroscopy or MRI on the material.

3. The method as defined in claim 1 further including the step of including an additive selected from the group of a catalyst, material, and a solvent.

4. The method as defined in claim 3 further including the step of adjusting parameters selected from the group of adjusting material and surfactant concentration, adjusting solvent concentration and adjusting catalyst concentration.

5. The method as defined in claim 1 wherein the step of distributing is selected from the group of injection, bubbling and adding appropriate parahydrogen containing material.

6. The method as defined in claim 1 further including the step of using the material to carry out at least one step of (a) enhancing the availability of hyperpolarized contrast agents in solution, in situ, or in vivo; (b) providing $H_2$ storage in solution; (c) enhancing the study of catalysis and reaction mechanisms in substances; (d) studying macromolecule structure, protein structure and molecular dynamics; (e) detecting peptides and proteins and studying their structures and dynamics; and (f) enhancing polarization transfer from other gasses selected from the group of helium, xenon, fluorine, deuterium, oxygen and para-$H_2O$.

* * * * *